United States Patent [19]

Boehm et al.

[11] Patent Number: 5,004,758

[45] Date of Patent: Apr. 2, 1991

[54] WATER SOLUBLE CAMPTOTHECIN ANALOGS USEFUL FOR INHIBITING THE GROWTH OF ANIMAL TUMOR CELLS

[75] Inventors: Jeffrey C. Boehm, King of Prussia, Pa.; Sidney M. Hecht, Charlottesville, Va.; Kenneth G. Holden, Malvern, Pa.; Randall K. Johnson, Ardmore, Pa.; William D. Kingsbury, Wayne, Pa.

[73] Assignee: SmithKline Beecham Corporation, Philadelphia, Pa.

[21] Appl. No.: 266,460

[22] Filed: Nov. 2, 1988

Related U.S. Application Data

[63] Continuation-in-part of Ser. No. 127,148, Dec. 1, 1987, abandoned.

[51] Int. Cl.$^5$ .................. A61K 31/47; C07D 491/22
[52] U.S. Cl. ................. 514/283; 514/233.2; 514/253; 544/125; 544/361; 546/48
[58] Field of Search .................. 546/48; 544/125, 361; 514/283, 233.2, 253

[56] References Cited

U.S. PATENT DOCUMENTS

| | | | |
|---|---|---|---|
| 4,342,776 | 8/1982 | Cragoe, Jr. et al. | 548/544 X |
| 4,473,692 | 9/1984 | Miyasaka et al. | 548/48 |
| 4,545,880 | 10/1985 | Miyasaka et al. | 204/158 R |
| 4,604,463 | 8/1986 | Miyasaka et al. | 544/125 |
| 4,775,759 | 10/1988 | Rice et al. | 546/44 |
| 4,820,816 | 4/1989 | Evans et al | 540/205 |
| 4,894,456 | 1/1990 | Wall et al. | 546/41 |

FOREIGN PATENT DOCUMENTS

| | | | |
|---|---|---|---|
| 0088642 | 9/1983 | European Pat. Off. | |
| 0227884 | 12/1984 | Japan | |
| 0195384 | 8/1987 | Japan | 546/48 |

OTHER PUBLICATIONS

Pan, et al., Chemical Abstracts, vol. 84: 115629p (1976).
Wani et al., *J. Med. Chem.*, 29, 2358–2363 (1986).
Nitta et al., Proc. 14th International Congr. Chemotherapy, Kyoto, 1985, Tokyo Univ., Tokyo Press, Anticancer Section 1, pp. 28–30.
H. M. Chang et al., Eds., World Scientific Publ. Co., Singapore, 1985, p. 377.
Department of Maxillo-facial Surgery, 9th People's Hospital, Shanghai, *Clin. J. Stomatology*, 13, 75 (1978).
Wani et al., *J. Med. Chem.*, 23, 554 (1980).
Wani et al., *J. Med. Chem.*, 30, 1774 (1987).

*Primary Examiner*—Diana Rivers
*Attorney, Agent, or Firm*—Carol G. Canter; Stuart R. Suter; Edward T. Lentz

[57] ABSTRACT

Water soluble camptothecin analogs, pharmaceutical compositions comprising such analogs, and a method of inhibiting the growth of tumor cells sensitive to such analogs in an animal in need thereof.

35 Claims, No Drawings

WATER SOLUBLE CAMPTOTHECIN ANALOGS USEFUL FOR INHIBITING THE GROWTH OF ANIMAL TUMOR CELLS

CROSS REFERENCE TO RELATED APPLICATIONS

This application is a continuation-in-part of Ser. No. 127,148 filed Dec. 1, 1987 which is abandoned.

BACKGROUND OF THE INVENTION

This invention relates to water soluble camptothecin analogs, a pharmaceutical composition comprising a tumor cell growth inhibiting amount of such an analog, and a method of inhibiting the growth of tumor cells sensitive to such an analog in an animal in need thereof.

The structure of the DNA helix within eukaryotic cells imposes certain topological problems that the cellular apparatus must solve in order to use its genetic material as a template. The separation of the DNA strands is fundamental to cellular processes such as DNA replication and transcription. Since eukaryotic DNA is organized into chromatin by chromosomal proteins, the ends are constrained and the strands cannot unwind without the aid of enzymes that alter topology. It has long been recognized that the advancement of the transcription or replication complex along the DNA helix would be facilitated by a swivel point which would relieve the torsional strain generated during these processes. Topoisomerases are enzymes that are capable of altering DNA topology in eukaryotic cells. They are critical for important cellular functions and cell proliferation.

There are two classes of topoisomerases in eukaryotic cells, type I and type II. Topoisomerase I is a monomeric enzyme of approximately 100,000 molecular weight. The enzyme binds to DNA and introduces a transient single strand break, unwinds the double helix (or allows it to unwind), and subsequently reseals the break before dissociating from the DNA strand.

Topoisomerase II consists of two identical subunits of molecular weight 170,000. Topoisomerase II transiently breaks both strands of the helix and passes another double-strand segment through the break.

Camptothecin is a water-insoluble, cytotoxic alkaloid produced by *Camptotheca accuminata* trees indigenous to China and *Nothapodytes foetida* trees indigenous to India. Camptothecin and a few close congeners thereof are the only class of compounds known to inhibit topoisomerase I.

Inhibition of topoisomerase II is the major target of important commercial oncolytic agents (e.g., etoposide, doxorubicin and mitoxantrone) as well as other oncolytic agents still undergoing development. Camptothecin (and its known congeners) have no effect on topoisomerase II and none of the known topoisomerase II inhibitors has any significant effect on topoisomerase I.

Camptothecin and its known topoisomerase I inhibiting congeners have not proven to be attractive for clinical drug development as cytolytic agents because of lack of clinical efficacy, unacceptable dose limiting toxicity, unpredictable toxicity, poor aqueous solubility, and/or unacceptable shelf life stability. Therefore, there is a need for topoisomerase I inhibiting agents which avoid the undesirable features of camptothecin and its known related topoisomerase I inhibiting congeners. The compounds of this invention fulfill such need.

Miyasaka et al., U.S. Pat. No. 4,604,463, issued Aug. 5, 1986 and assigned to Yakult Honsha, K. K., disclose camptothecin derivatives of the formula:

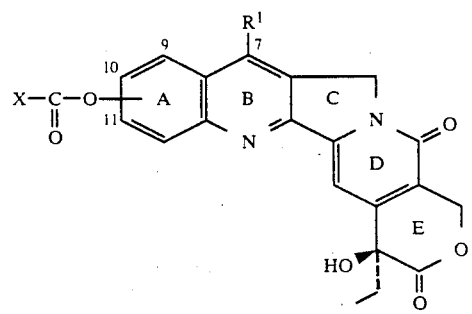

wherein $R^1$ is a hydrogen atom, a halogen atom or an alkyl group with 1-4 carbon atoms and X is a chlorine atom or where $-NR^2R^3$ where $R^2$ and $R^3$ are the same or different and each represents a hydrogen atom, a substituted or unsubstituted alkyl group with 1-4 carbon atoms or a substituted or unsubstituted group selected from the group consisting of cyclopentyl, cyclohexyl, N-methylpiperidyl-(4), 2-pyrrolidyl, phenyl, tolyl, xylyl, pyridyl-2 and 2-methylpyridyl-(4), with the proviso that when both $R^2$ and $R^3$ are the substituted or unsubstituted alkyl groups, they may be combined together with the nitrogen atom, to which they are bonded, to form a heterocyclic ring selected from the group consisting of pyrrolidine, piperidine, 2-oxapyrrolidine, morpholine, thiomorpholine and 4-$R^4$ piperidine rings in which $R^4$ is a hydrogen atom, a substituted or unsubstituted alkyl group with 1-4 carbon atoms or a substituted or unsubstituted phenyl group and wherein the grouping $-O-CO-X$ is bonded atom located in any of the 9-, 10- and 11-positions in the ring A, and ammonium salts or alkali metal salts thereof. Miyasaka et al. also state that such camptothecin derivatives are useful as antitumor medicaments possessing strong antitumor activity with reduced toxicity.

Miyasaka et al., U.S. Pat. No. 4,473,692, issued Sept. 25, 1984 and assigned to Yakult Honsha, K. K., disclose camptothecin derivatives of the formula:

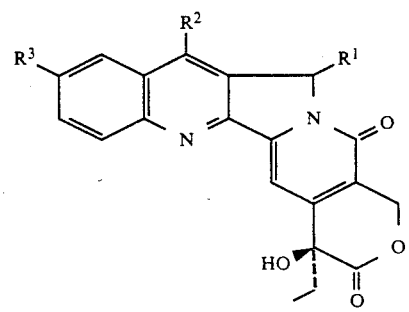

wherein $R^1$ is a hydrogen atom, a straight or branched $C_1-C_{30}$ alkyl group, a $C_5-C_8$ hydroxyl group, a $C_1-C_{30}$ alkoxy group or a $C_1-C_{17}$ acyloxy group, $R^2$ is a hydrogen atom, a straight or branched $C_1-C_{30}$ alkyl group, a $C_5-C_8$ cycloalkyl group, a phenylalkyl group, a naphthylalkyl group, a hydroxymethyl group, a carboxymethyl group or a $C_1-C_{17}$ acyloxymethyl group, and $R^3$ is $XR'$ where $R'$ is a hydrogen atom, a straight or branched $C_1-C_{30}$ alkyl group or a $C_1-C_{17}$ acyl group and X is an oxygen atom or a sulfur atom or wherein $R'$ is a nitro group, an amino group, a $C_1$-$C_8$ alkylamino group, a $C_1$-$C_{17}$ acylamino group or a halogen atom, with the proviso that when both $R^1$ and $R^2$ are hydrogen atoms, $R^3$ is not hydroxy, methoxy or acetoxy. Miyasaka et al also state that the above camptothecin derivatives have high antitumor activity with slight toxicity.

Miyasaka et al, U.S. Pat. No. 4,545,880, issued Oct. 8, 1985 discloses a method for the preparation of camptothecin derivatives of the formula:

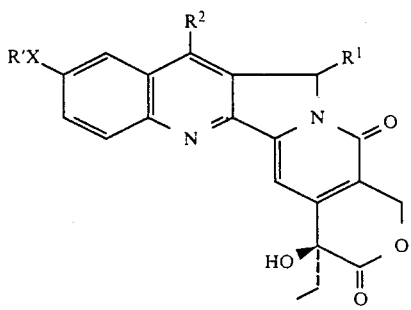

wherein $R^1$ stands for a hydrogen atom, an alkyl group, a hydroxyl group, an alkoxy group or an acyloxy group, $R^2$ for a hydrogen atom, an alkyl group, an aralkyl group, a hydroxymethyl group, carboxymethyl group or an acyloxymethyl group, $R'$ for a hydrogen atom, an alkyl group or an acyl group and X for an oxygen atom or a sulfur atom.

Yakult Honsha K. K., European Patent Application Publication Number 0,088,642,A2, published Sept. 14, 1983, disclose camptothecin derivatives of the formula:

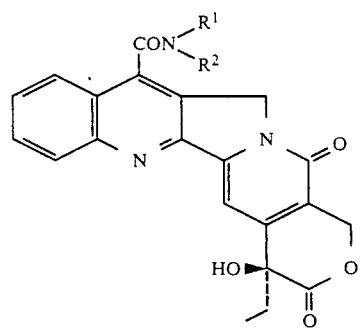

wherein $R^1$ and $R^2$ each stands for a hydrogen atom, a substituted or unsubstituted alkyl group, a substituted or unsubstituted aralkyl group or a substituted or unsubstituted aryl group and $R^1$ and $R^2$, taken together with the nitrogen atom to which they are attached, may form a cyclic group. Yakult Honsha, K. K. state that such compounds are useful as pharmaceutical intermediates for antitumor agents.

Wani et al., J. Med. Chem., 29, 2358-2363 (1986), disclose the L-1210 mouse leukemia assay antitumor activity of various camptothecin analogs including 9-nitro-20(S)-camptothecin, 9-amino-20(S)-camptothecin, 9-nitro-10-methoxy-20(S)-camptothecin, 9-amino-10-methoxy-20(S)-camptothecin, 9-nitro-10-hydroxy-20(S)-camptothecin and 9-acetamido-10-hydroxy-20(S)-camptothecin.

Nitta et al., Proc. 14th International Congr. Chemotherapy, Kyoto, 1985, Tokyo Univ., Tokyo Press, Anticancer Section 1, p. 28-30, disclose that a compound called CPT-11 has a profile of activity in preclinical tumor models. CPT 11 is a water soluble camptothecin analog with a 4-(piperidino)-piperidine side chain joined through a carbamate linkage at C-10 of 10-hydroxy-7-ethyl camptothecin.

Although camptothecin is beset by bladder toxicity and unpredictable toxicity to proliferating tissues which preclude its use, 10-hydroxycamptothecin, appears, from the Chinese literature, to retain human solid tumor activity with much reduced toxicity. See, Xu Bin and Yang Jin Long, "Advances in Chinese Medicinal Materials Research", H. M. Chang et al., Eds., World Scientific Publ. Co., Singapore, 1985, p. 377, which discuss the results of Phase I and Phase II clinical trial of 10-hydroxycamptothecin in 253 patients in several types of human solid tumors.

Department of Maxillo facial surgery, 9th People's Hospital, Shanghai, Clin. J. Stomatology, 13, 75 (1978), discusses Phase II clinical trials of camptothecin and 10 hydroxycampothethecin in several types of human solid tumors.

Wani et al., J. Med. Chem., 23, 554 (1980), disclose the synthesis of various synthetic analoqs of camptothecin and 10-hydroxycamptothecin including an analog in which there is a diethylaminoethyl ether at C-10.

Wani et al., J. Med. Chem., 30, 1774 (1987), disclose the synthesis of various 11-substituted camptothecin analogs including cyano, nitro, amino, dimethylamino, formyl, aminomethyl, and hydroxymethyl. Wani et al. report that, among these analogs, only the 11-cyano, 11-nitro and 11-amino camptothecin analogs were active in an assay for antitumor activity. Notably, the 11-aminomethyl analog and its hydrochloride salt were reported to be inactive.

SUMMARY OF THE INVENTION

This invention relates to a compound of the formula

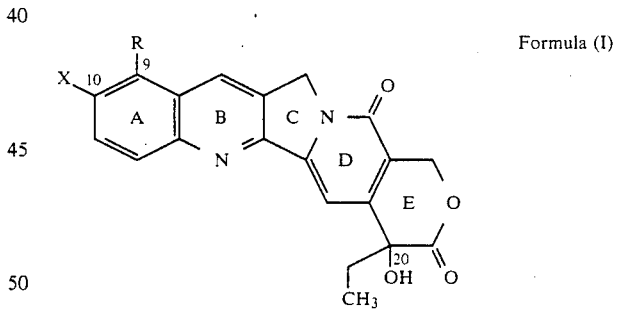

Formula (I)

wherein:

X is hydroxy; hydrogen; —$CH_2NH_2$; or formyl;

R is hydrogen when X is $CH_2NH_2$ or formyl; or R is —CHO or —$CH_2R^1$ when X is hydrogen or hydroxy;

$R^1$ is —O—$R^2$; —S—$R^2$; —$CH_2NH_2$; —N—$R^2(R^3)$; or —N⊕—$R^2(R^3)(R^4)$, provided that when $R^1$ is —N⊕—$R^2(R^3)(R^4)$ the compound is associated with a pharmaceutically acceptable anion;

$R^2$, $R^3$ and $R^4$ are the same or different and are selected from H; $C_{1-6}$ alkyl; $C_{2-6}$ hydroxyalkyl; $C_{1-6}$ dialkylamino.; $C_{1-6}$ dialkylamino-$C_{2-6}$ alkyl; $C_{1-6}$ alkylamino-$C_{2-6}$ alkyl; $C_{2-6}$ aminoalkyl or a 3-7 member unsubstituted or substituted carbocyclic ring; and when $R^1$ is —N—$R^2(R^3)$, the $R^2$ and $R^3$ groups may be combined together with the nitrogen atom to which they are bonded to form heterocyclic ring provided that such heterocyclic ring is selected from morpholino, N-methylpiperazinyl, or 4'-piperidinopiperidinyl which may contain additional heteroatoms;
or a pharmaceutically acceptable salt, hydrate or solvate thereof.

This invention also relates to a compound of the formula

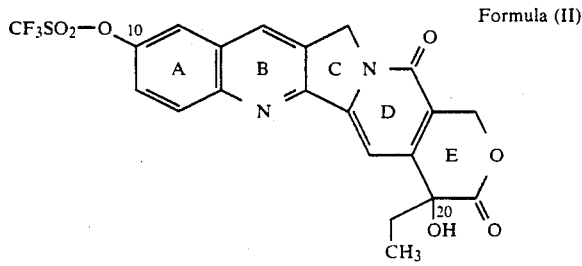

Formula (II)

The compound of Formula (II) is useful in preparing the compounds of Formula (I).

By the term "carbocyclic ring" is meant a fully saturated, partially saturated or fully unsaturated ring system.

Preferred compounds of Formula (I) include those wherein when X is hydroxy, R is dimethylaminomethyl, N-morpholinomethyl, N-methylpiperazinylmethyl, (4'-piperidine)N-piperidinylmethyl, (2'-hydroxyethyl)aminomethyl, trimethylammoniummethyl, cyclohexylaminomethyl, N-methylanilinomethyl, ethoxymethyl, cyclopropylaminomethyl, N,N-dimethylamino ethyloxymethyl, N,N-dimethylaminoethylthiomethyl, N,N-dimethylaminoethylaminomethyl, cyanomethyl, aminoethyl or formyl. Preferred compounds of Formula (I) also include those compounds wherein when R is hydrogen, X is cyano, formyl or aminomethyl. Additional preferred compounds of Formula (I) are those wherein X is hydrogen and R is dimethylaminomethyl or N morpholinomethyl. Especially preferred are the compounds of Formula (I) wherein R is dimethylaminomethyl, particularly the S-isomer form thereof.

This invention also relates to a pharmaceutical composition comprising an effective, tumor cell growth-inhibiting amount of a compound of Formula (I) and an inert pharmaceutically acceptable carrier or diluent.

This invention also relates to a method of inhibiting the growth of tumor cells sensitive to a compound of Formula (I) which comprises administering to an animal, including a human, afflicted with said tumor cells, an effective, tumor cell growth inhibiting amount of such compound.

It is recognized that due to the asymmetric carbon atom in the E ring of the compounds of Formula (I) (i.e., carbon atom number 20), optical isomers will exist. The S-isomer is the preferred isomer, however the R-isomer and racemic mixture (racemate) are also included within the scope of the compounds of Formula (I).

Pharmaceutically acceptable salts and their preparation are well-known to those of skill in the art. Preferred pharmaceutically acceptable salts of compounds of Formula (I) include acetate, methane sulfonate and hydrochloride, such as mono- and di-hydrochloride, as well as alkali metal salts of compounds of Formula (I), such as sodium, wherein the E-ring lactone has been subjected to basic hydrolysis.

Pharmaceutically acceptable anions of quatenary salts are well-known to those of skill in the art. Preferred pharmaceutically acceptable salts of compounds of Formula (I) where $R^1$ is $-N^+-R^2(R^3)(R^4)$ include methane sulfonate and chloride.

The compounds of Formula (I) may form hydrates or solvates. It is known to those of skill in the art that charged compounds form hydrated species when lyophilized with water, or form solvated species when concentrated in a solution with an appropriate organic solvent.

DETAILED DESCRIPTION OF THE INVENTION

The compound of Formula (II) may be prepared according to the procedure outlined in Example 22.

The compounds of Formula (I) can be prepared from 10-hydroxycamptothecin via a Mannich reaction. Condensation of 10-hydroxycamptothecin with formaldehyde and a primary or secondary amine (Mannich reaction) gives all the compounds of Formula (I) except the compound where X is hydrogen; cyano; or formyl and $R^1$ is $-N-R^2(R^3)$ and $R^2$ and $R^3$ are the same and are H. Alternatively, 10-hydroxycamptothecin can be formylated (Duff reaction) to give 9-formyl-10-hydroxycamptothecin which can then undergo condensation with amines followed by chemical reduction with sodium cyano borohydride or catalytic reduction (Pd/C, $H_2$) to give products analogous to those derived via the Mannich reaction as well as the compound of Formula (I) wherein $R^1$ is $-N-R^2(R^3)$ and $R^2$ and $R^3$ are the same and are H. Compounds of Formula (I) where $R^1$ is $-N^+-R^2(R^3)(R^4)$ and $R^2$, $R^3$ and $R^4$ are not H are obtained by treatment of the corresponding compounds of Formula (I) in which $R^1$ is $-N-R^2(R^3)$ with an alkylating agent. The Mannich reaction is disclosed by Magarian et al., *J. Pharm. Sci.*, 56, 987 (1967). The Duff reaction is disclosed by Duff et al., *J. Chem. Soc.*, 547 (1941).

Compounds of Formula (I) where $R^1$ is $O-R^2$ or $S-R^2$ can be prepared from 9-dimethylaminomethyl-10-hydroxycamptothecin or its salt by heating with the appropriate alcohol or thiol in an inert solvent such as dimethylformamide. When the free base is used, a small amount of strong acid, such as hydrochloric acid, is added. Such derivatives can also be formed directly in the Mannich reaction when the alcohol or thiol is included in the reaction mixture and a strong acid is added, or the amine component is in the form of a strong acid salt.

The compounds of Formula (I) where X is hydrogen, cyano, formyl or aminomethyl can be prepared from the compound of Formula (II) by palladium-catalyzed cabonylation. Palladium-catalyzed carbonylation of aryl triflates is disclosed by Cacchi et al., *Tetrahedraon Letters*, 27, 3931, 5541, (1986): Petrakis et al., *J. Amer. Chem. Soc.*, 109, 2831 (1987) and Chatani et al., *J. Org. Chem.*, 51, 4714 (1986).

The starting material for the preparation of compounds of Formula (I), i.e., 10 hydroxycamptothecin, is a natural product found in the same plant as camptothecin [See, Wani et al., *J. Org. Chem.*, 34, 1364 (1969)]. 10-methoxycamptothecin has also been isolated from the same plant as camptothecin and can be converted to 10-hydroxycamptothecin by refluxing with hydrogen bromide. Camptothecin itself can also be converted to 10-hydroxycamptothecin by reduction of the pyridine ring followed by oxidation with lead tetraacetate [See, Yakult Honsha K. K., Japanese Patent Application No. 9005188, filed June 30, 1982]. Racemic 10-hydroxycamptothecin can also be prepared by the method of Wani et al., *J. Med. Chem.*, 23, 554 (1980). A large number of methods for the total synthesis for camptothecin have been reported. See, e.g., Hutchinson, *Tetrahedron*, 37, 1047 (1981), and Suffness and Coldel, "The Alkaloids. Chemistry and Pharmacology", Brossi, A., ed., Vol. 25, Academic Press, Orlando, Fla., 73 (1985), for reviews. The most practical route (hereinafter referred to as the Wani route) for producing camptothecin which is racemic at the carbon on the 20 position is described by Wani et al., *J Med Chem.*, 23, 554 (1980).

Utility of Compounds of Formula (I)

a: Cytotoxicity

The acetate salt of the compound of Formula (I) wherein R is dimethylaminomethyl (S isomer) (hereinafter referred to as "Compound No. 1S") demonstrated potent antiproliferative activity in a variety of cultured cell lines (Table 1). In a series of eight cultured human colon tumor cell lines, Compound No. 1S was quite consistent in its cytotoxic potency. For a brief exposure (2 hours) to the drug, the 50 percent inhibitory concentration ranged from 0.12–2.1 µg/ml. If the drug was left in the culture medium for the full 7-day period over which cells were allowed to proliferate, the $IC_{50}$ values ranged from 3.9–75 ng/ml.

Three rodent tumor cell lines and two "normal" rodent cell lines were also evaluated for sensitivity to Compound No. 1S. The K12/Tr rat colon carcinoma and the rat kidney and intestinal epithelial cell lines were evaluated in the same experiment using the endpoint used in the human colon tumor cell experiments. These rodent cells were similar in sensitivity to the least sensitive human colon tumor cell lines, CACO-2 and WiDR. The mouse tumor cell lines, L1210 leukemia and B16 melanoma, were no more sensitive to the Compound No. 1S than the human colon tumor cell lines. In fact, the B16 melanoma cell line seemed to be considerably less sensitive than the other cell lines tested. Notably, B16 and L1210 are both quite sensitive to Compound No. 1S in vivo in therapeutic trials in tumor bearing mice.

The protocol used to evaluate the cytotoxicity of Compound No. 1S in the cell lines listed in Table 1 was generally as follows:

The cell lines are used and maintained as monolayer cultures in Minimal Essential Media (Grand Island Biological Co., Grand Island, N.Y.) supplemented with 10% fetal calf serum in a 5% $CO_2$ humidified incubator at 37° C. Various concentrations of a Formula (I) compound under sterile conditions were allowed to react for 2 hours followed by aspiration of medium or were exposed continuously. Plates are incubated for 7 days at 37° C. in a $CO_2$ incubator. Medium was aspirated and cells were fixed and stained with ethanol and Geisma stain. The surviving cell population was determined by scanning the plates with an image analyzer. The percent inhibition of proliferation was determined relative to cells incubated in the absence of drug and the 50 percent inhibitory concentration ($IC_{50}$) was determined by interpolation.

TABLE 1

Cytotoxicity of Compound No. 1S to Tumor Cells in Culture

| | $IC_{50}$ (µg/ml) | |
|---|---|---|
| Cell Line | 2 Hr. Exposure | Continuous Exposure |
| Human Colon Tumor Cell Lines | | |
| SW-620 | 0.12 | 0.0065 |
| SKCO-1 | 0.23 | 0.0039 |
| SW-948 | 0.26 | 0.016 |
| DLD-1 | 0.44 | 0.015 |
| LOVO | 0.58 | 0.0097 |
| HT-29 | 0.58 | 0.016 |
| CACO-2 | 1.7 | 0.075 |
| WiDR | 2.1 | 0.025 |
| Rodent Tumor Cell Lines | | |
| L1210 Leukemia | 1.4 | n.d. |
| K12/Tr Colon Carcinoma | 3.9 | 0.084 |
| B16 Melanoma | n.t.* | 0.62 |
| Rodent "Normal" Cell Lines | | |
| NRK52E (rat kidney epithelium) | 1.2 | 0.052 |
| IEC-6 (rat intestinal epithelium) | 3.9 | 0.017 |

*n.t. = not tested

A variety of Formula (I) compounds were evaluated for cytotoxicity against L1210 leukemia cells growing in suspension culture (Table 2). Cells were exposed continuously upon cloning into medium containing 0.2 percent Noble agar. After incubation at 37° C. in a $CO_2$ incubator for 3 days, colonies were stained with viable cell specific formazan stain and, 24 hours later, were enumerated by a colony counter (Biotran II, New Brunswick Scientific Co., Edison, N.J.) adjusted to identify colonies of more than 50 cells. The concentration which reduced cloning efficiency by 50 percent $IC_{50}$) was determined by interpolation. Formula (I) compounds had $IC_{50}$ values of 12 to 690 nM, i.e., $IC_{50}$ values which were indicative of cytotoxic activity. The related natural product, 10-hydroxy-camptothecin, had an $IC_{50}$ of 18 nM. Cytotoxic compounds of Formula (I) are potent inhibitors of purified topoisomerase I. As indicated in the following section related to in vivo activity, a number of Formula (I) compounds, although generally less cytotoxic than 10-hydroxycamptothecin, had antitumor activity against L1210 leukemia in vivo which was equivalent or superior to that of 10-hydroxycamptothecin. For example, Compound No. 1S was about 3-fold less potent than 10-hydroxycamptothecin with respect to cytotoxic potency against L1210 leukemia cells in vitro, but exhibited in vivo tumor cell growth inhibiting activity which was generally superior to 10-hydroxycamptothecin in a variety of rodent transplantable tumor models.

TABLE 2

Activity of Formula (I) Compounds Against L1210 Leukemia in vitro and in vivo in Mice Bearing ip-implanted Tumors Formula (I)

| Compound Number | R | X | In Vitro Activity $IC_{50}$ (nM) | In Vivo Antitumor Activity MTD (mg/kg) | ILS (%) |
|---|---|---|---|---|---|
| 10-Hydroxycamptothecin | —H | hydroxy | 18 | 9 | 94 |
| 1S | —$CH_2N(CH_3)_2$ (acetate salt) | hydroxy | 56 | 15 | <200 |
| 2S | —CHO | hydroxy | 260 | 42 | 75 |
| 3S | —$CH_2N^{\oplus}(CH_3)_3$ | hydroxy | 150 | 42 | >200 |
| 4S | —$CH_2NHCH_2CH_2OH$ | hydroxy | 250 | 42 | 75 |
| 5S | —$CH_2N$(morpholino) | hydroxy | 370 | 100 | 83 |
| 6S | —$CH_2N$(N-methylpiperazino) | hydroxy | 72 | 75 | >200 |
| 7S | —$CH_2N$(4-piperidinopiperidino) | hydroxy | 270 | >42* | 44 |
| 8S | —$CH_2NH$-cyclopropyl | hydroxy | 130 | 25 | 131 |
| 9S | —$CH_2N(CH_3)$-phenyl | hydroxy | 69 | 42 | 112 |
| 10S | —$CH_2OCH_2CH_3$ | hydroxy | 48 | 25 | 131 |
| 11S | —$CH_2NH$-cyclohexyl | hydroxy | 56 | 25 | >200 |
| 12S | —$CH_2NHCH_2CH_2N(CH_3)_2$ | hydroxy | 49 | >42* | 94 |
| 13S | —$CH_2OCH_2CH_2N(CH_3)_2$ | hydroxy | not tested | 42 | 188 |
| 14S | —$CH_2SCH_2CH_2N(CH_3)_2$ | hydroxy | 12 | 42 | 112 |
| 15S | —$CH_2N(CH_3)_2$ | hydrogen | 65 | 15 | 88 |
| 16S | hydrogen | cyano | 80 | 3 | 100 |
| 17S | —$CH_2CN$ | hydroxy | 400 | 12 | >200 |
| 18S | —$CH_2N$(morpholino) | hydrogen | 690 | 13 | 144 |
| 19S | hydrogen | —CHO | 62 | not tested | |
| 20S | hydrogen | —$CH_2NH_2$ | 90 | 92 | 112 |
| 21S | —$CH_2N(CH_3)_2$ | hydroxy | not tested | 54 | >200 |

TABLE 2-continued

Activity of Formula (I) Compounds Against L1210 Leukemia in vitro and in vivo in Mice Bearing ip-implanted Tumors

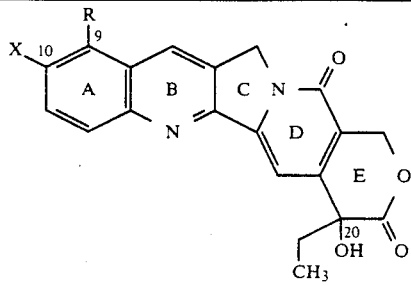

Formula (I)

| Compound Number | R | X | In Vitro Activity IC$_{50}$ (nM) | In Vivo Antitumor Activity MTD (mg/kg) | ILS (%) |
|---|---|---|---|---|---|
| | (sodium salt) | | | | |
| 22S | —CH$_2$CH$_2$NH$_2$ | hydroxy | 360 | 100 | 75 |

For in vivo studies L1210 cells were implanted i.p. (10$^6$ per mouse) and drugs were administered i.p. on Days 1 and 5. Increase in lifespan (ILS) was based on median survival time of groups of 6 mice treated at the maximally tolerated dose of the drugs.
*Highest dose tested (degree of activity likely greater at a higher dose level)
For in vitro studies L1210 cells were grown in suspension culture and exposed to drugs continously upon cloning of cells into soft agar. Cloning efficiency was determined. The 50 percent inhibitory concentration (IC$_{50}$) was determined by interpolation.
All compounds listed above were effective inhibitors of topoisomerase I and purified from human colon cancer cells; 50% inhibition of the enzyme activity was seen at concentrations of $\leq 3$ $\mu$M.

b. In Vivo Tumor Cell Growth Inhibition

Compounds of Formula (I) were initially evaluated for in vivo antitumor activity in mice bearing intraperitoneally (ip) implanted L1210 leukemia (Table Compound No. 1S and Compounds No. 4S-13S prolonged the lifespan of tumor bearing mice by >40 percent at their respective maximally tolerated dose levels. Three compounds—Compounds No. 1S, 6S and 11S—were particularly active, prolonging lifespan by >200 percent and producing long-term, tumor-free survivors. A number of compounds had activity superior to that of the natural product, 10-hydroxycamptothecin, to which Formula (I) compounds are structurally related. For two of the compounds—Compounds No. 7S and 13S—the highest dose tested was not toxic, thus these compounds may have greater activity at higher dose levels. Nevertheless, at the dose levels tested these compounds were active.

Based on its high degree of activity and potency in vivo (i.e., low maximally tolerated dose) Compound No. 1S was evaluated in a number of transplanted murine tumor models. Compound No. 1S has a high degree of activity at its maximally tolerated dose in a variety of animal tumor models, including leukemias and solid tumors of diverse histiotype. The spectrum of activity of Compound No. 1S is summarized in Table 3. A high level of activity was seen in the majority of tumor models with only one of the models, ip colon carcinoma 26 proving to be almost totally refractory to the drug. Also two of the sc models, colon carcinoma 26 and Madison lung carcinoma, proved to be somewhat refractory to the drug; i.e., in these models, modest activity, i.e., >70 percent inhibition of tumor growth, was evident when mice bearing subcutaneous tumors were treated with Compound No. 1S. In the other sc tumor models, high activity (greater than 90 percent inhibition) was exhibited. Notably, Compound No. 1S administered ip demonstrated high activity not only against ip tumor models but in mice inoculated with tumors intravenously (iv) or subcutaneously (sc). Curative activity was evident in certain tumor models including ip- and iv-implanted P388 and L1210 leukemias and iv- and sc-implanted Lewis lung carcinoma. The level and spectrum of activity of Compound No. 1S in animal tumor models compares favorably with the most broadly effective of the known antitumor drugs such as cyclophosphamide, cisplatin and doxorubicin.

The results of these transplanted murine tumor model studies are summarized in greater detail in Table 4 which shows the prolongation of lifespan (ILS) or percent inhibition of measurable (i.e., subcutaneous) solid tumor growth achieved with optimal doses and optimal schedules of administration of Compound No. 1S. Also shown in Table 4 are results obtained in comparative studies on these tumor models with the natural product parent compounds, camptothecin and 10-hydroxycamptothecin. These results were achieved with ip or iv administration of Compound No. 1S on an intermittent schedule (i.e., every fourth or seventh day). In some instances, the results were obtained with an optimal treatment regimen in which Compound No. 1S was administered on a split dose regimen (every 3 hours times 4) on each day of treatment as is described in more detail below. Camptothecin and 10-hydroxycamptothecin were always administered as suspensions ip due to their insolubility in aqueous vehicles.

It is evident from Table 4 that all three compounds have a broad spectrum of activity in animal tumor models. Superior activity for Compound No. 1S is evident in several tumor models including: ip L1210 leukemia, ip B16 melanoma, iv P388 leukemia, iv L1210 leukemia, sc Lewis lung carcinoma, sc B16 melanoma, sc B16 melanoma/F10 subline, sc colon carcinoma 51, and sc Madison lung carcinoma. 10-Hydroxycamptothecin is quite active in ip implanted tumor models but has inferior activity in tumor models in which the tumor is implanted at a site distant to the site of drug administration; this drug has, at best, minimal activity in sc-implanted solid tumor models. This is likely not due to the poor solubility of 10-hydroxycamptothecin since camptothecin is equally insoluble but is quite active in certain sc tumor models. It is possible that the aromatic hydroxyl group of 10-hydroxycamptothecin is susceptible to first pass conjugation and biliary excretion and, thus, the compound does not achieve adequate concentrations in the systemic circulation. Notably, Compound No. 1S, which also has a 10-hydroxyl group, is highly active in sc and iv tumor models. This may be due to the presence of the basic side chain in the 9 position of Compound No. 1S which may inhibit metabolism of the 10-hydroxyl group by steric hindrance, hydrogen bonding or internal salt formation. 10-Hydroxycamptothecin is highly active in ip colon carcinoma 26 which is insensitive to Compound No. 1S and minimally sensitive to camptothecin. However, the same tumor is refractory to 10-hydroxycamptothecin when implanted sc yet has modest sensitivity to Compound No. 1S in this setting.

In addition to the high degree and broad spectrum of activity of Compound No. 1S as demonstrated in Table 4, the compound also would appear to retain full antitumor activity when administered orally. This was demonstrated in mice bearing sc-implanted Lewis lung carcinoma and is described in detail below. Another characteristic of Compound No. 1S is its retention of activity in sublines of P388 leukemia which display resistance to multiple antitumor drugs as described below. As a major problem in cancer chemotherapy is emergence of resistant cell populations which fail to respond to initially effective drug regimens as well as second-line treatment regimens, the availability of drugs to which resistant cells are not cross-resistant should have a significant impact on the management of cancer.

The activity of Compound No. 1S in each of the tumor models which have been tested is described in more detail in the following sections.

ip Tumor Models

The activity of Compound No. 1S administered ip or sc on various treatment schedules to mice bearing ip-implanted tumors is shown in Table 5. The data demonstrates the dose-dependency of the antitumor effect of Compound No. 1S in six ip implanted tumor models.

P388 Leukemia: When given ip on Days 1 and 5 to mice bearing ip P388 leukemia, Compound No. 1S produced 200 percent ILS with 4/6 long term survivors (cures) at its maximally tolerated dose of 15 mg/kg. Lower doses were also highly effective with increases in lifespan of 125 and 92 percent. This high degree of activity was confirmed in another experiment described later (see Table 8) in which the maximally tolerated dose produced 228 percent ILS with 2/6 long term survivors. Thus, Compound No. 1S had curative activity in mice bearing ip P388 leukemia.

L1210 Leukemia: When given ip on Days 1 and 5, Compound No. 1S was reproducibly active in mice bearing ip L1210 leukemia. In the representative experiment shown in Table 5, there was 219 percent ILS with 2/6 cures at the maximally tolerated dose of 15 mg/kg. Good activity was seen at two lower doses as well. Compound No. 1S was evaluated on this schedule in eight additional dose response studies. The percent ILS and long term survivors obtained at the maximally tolerated doses in these experiments were: 44% (0/6), >300% (5/6), 119% (0/6), 156% (1/6), 138% (0/6), 156% (2/6), 350% (2/6) and 138% (1/6). Thus, in 8/9 experiments Compound No. 1S produced >100% ILS and in 6/9 experiments there were long term survivors.

B16 Melanoma: In this tumor model, in which Compound No. 1S was markedly superior to camptothecin and 10-hydroxycamptothecin (see Table 4), the drug produced 52 percent ILS at its maximally tolerated dose of 15 mg/kg given ip on Days 1, 5, 9 and 13. This result was confirmed in a second experiment in which the highest dose tested, 9.6 mg/kg, produced 130 percent ILS.

B16 Melanoma/F10 Subline: The F10 subline of B16 melanoma is a highly metastatic subline of this tumor which was selected by cloning. Compound No. 1S produced 105 percent ILS at its maximally tolerated dose of 15 mg/kg given ip on Days 1, 5, 9 and 13. Activity, as indicated by increases in lifespan of >40 percent, was evident at two lower doses as well.

M5076 Sarcoma: The M5076 sarcoma is a metastatic reticulum cell sarcoma which arose in the ovary of a C57B1/6 mouse and was established as a transplanted tumor. This tumor, implanted ip, was sensitive to Compound No. 1S when the drug was administered sc as well as by ip drug administration. The degree of activity was virtually identical, 98 percent ILS and 105 percent ILS, by the two routes of administration on the split-dose schedule of every 3 hours×4 on Days 1, 5 and 9. This schedule, as described below, appears to be optimal for Compound No. 1S in a number of tumor models. Compound No. 1S was evaluated in 3 additional dose-response studies in mice bearing ip M5076 sarcoma; in these studies the drug was given as a single dose on Days 1, 5 and 9 ip (75 percent ILS with 1/8 cures), as a single dose on Days 1, 5, 9 and 13 ip (71 percent ILS with ½ cures), and as a single dose on Days 1, 5, and 9 sc (57 percent ILS). As in iv and sc tumor models (as described below), Compound No. 1S appears to be most effective in ip M5076 sarcoma when administered on a split-dose treatment regimen. Nevertheless, regardless of schedule of administration, Compound No. 1S is reproducibly active in this tumor model.

Colon Carcinoma 26: Colon carcinoma 26 is a highly invasive and metastatic undifferentiated colon tumor model. This tumor, on the schedule tested, proved to be refractory to a maximally tolerated dose of Compound No. 1S.

iv Tumor Models

The activity of Compound No. 1S administered ip or iv to mice bearing systemic (iv inoculated) leukemias or Lewis lung carcinoma is shown in Table 6. The dose-responsiveness and schedule dependency of Compound No. 1S is clearly demonstrated by these studies. In each of the three tumor models, Compound No. 1S demonstrated curative activity.

P388 Leukemia: P388 leukemia is generally much less drug sensitive when implanted iv than when inoculated ip. However, Compound No. 1S was highly active against iv P388 leukemia whether given at its maximally tolerated dose on Days 1 and 5 ip (279 percent ILS with 2/6 cures) or iv (250 percent ILS with 2/6 cures). In a third experiment in this tumor model, Compound No. 1S produced 125 percent ILS with 1/6 cures at a maximally tolerated dose of 15 mg/kg given ip on Days 1 and 5.

L1210 Leukemia: Compound No. 1S proved to be reproducibly and highly active against iv implanted L1210 leukemia. Extensive schedule dependency studies were performed in this tumor model with the drug administered iv. As demonstrated in Table 6, administration on a split dose regimen resulted in a higher degree of activity over a broader dosage range. Curative activity was seen when the drug was administered iv on Days 2 and 6 as a single dose or as four doses at 3 hour intervals. In addition to the data shown in Table 6, there are 10 dose-response studies with iv-administered Compound No. 1S in mice bearing iv L1210 leukemia. The results are as follows: Days 2 and 6, 171 percent ILS with 2/6 cures; 4 treatments at 3-hour intervals on Days 2 and 6, >300 percent ILS with 6/6 cures; three treatments at 6-hour intervals on Days 2 and 6, 200 percent ILS with 2/7 cures; 2 treatments at 12-hour intervals on Days 2 and 6, 229 percent ILS with 2/7 cures; single treatments on Days 2 through 6, 143 percent ILS and 129 percent ILS; 2 treatments at 12 hour intervals on Days 2 through 6, 193 percent ILS and 171 percent ILS; a single dose on Day 2, 114 percent ILS; and 4 treatments at 3 hour intervals on Day 2, 244 percent ILS with 1/6 cures. Compound No. 1S would appear to be most effective when administered on an every 3-hour schedule. It is less effective when given daily than when given every fourth day. The optimal schedule from these studies was used for certain solid tumors as discussed above for ip M5076 sarcoma and as described below. In a variety of tumor systems the degree of activity is increased and the effective dosage range is broader when Compound No. 1S is given on a split dose (i.e. every 3 hours times 4) schedule.

Lewis Lung Carcinoma: Lewis Lung carcinoma is a highly metastatic, undifferentiated lung cancer which has been used extensively for drug evaluation. This tumor model is refractory to many of the established antitumor drugs and, when used as a screening system, identified very few compounds as active. Compound No. 1S is curative in this chemorefractory tumor model wherein the tumor is inoculated iv resulting in tumor nodules in the lungs. Curative activity in this tumor model is an unusual finding.

As evident from all three of the iv inoculated tumor models, Compound No. 1S is quite effective against systemic tumors when administered ip as well as iv.

sc Tumor Models

Compound No. 1S was evaluated in ten solid tumor models in which tumors were implanted sc and drug was administered ip, iv or orally (po). In these models antitumor activity is assessed by degree of inhibition of tumor growth at the site of tumor implantation. Tumors are measured generally 2 to 3 weeks following tumor implantation when large tumors (>500 mm³) are evident in untreated control animals. For highly metastatic solid tumors survival time can also be used as a measure of drug activity. For less metastatic tumor models survival time of untreated animals is highly variable and animals can survive for long periods with extremely large tumors which often ulcerate and become infected. Compound No. 1S was highly effective in 8 of the 10 sc solid tumor models, inhibiting tumor growth by over 90 percent at its maximally tolerated dose (Table 7). Complete inhibition of tumor growth in the highly metastatic tumors including Lewis lung carcinoma, B16 melanoma, B15 melanoma/F10 subline, and M5076 sarcoma was accompanied by prolongation of lifespan. Even in the less responsive tumor models, Madison lung carcinoma and colon carcinoma 26, Compound No. 1S had some tumor growth inhibitory activity with >70 per cent inhibition evident at the maximally tolerated dose.

Lewis Lung Carcinoma: This highly metastatic lung tumor was the most sensitive to Compound No. 1S of the tumor models tested. This is an unusual finding since Lewis lung carcinoma has been widely used in the study of antitumor drugs and is refractory to the majority of the known antitumor drugs. When given ip on Days 1, 5, 9 and 13, Compound No. 1S completely inhibited the growth of Lewis lung carcinoma in virtually all mice treated at 15 or 9 mg/kg. At the maximally tolerated dose, 4 of 8 mice were cured. At the time of tumor measurement (Day 14), tumors in untreated controls averaged 1685 mm³ in volume. In a second experiment Compound No. 1S was administered iv and po on Days 1, 5 and 9. By both routes of administration there was 99 percent inhibition of tumor growth (TGI) with half or more of the animals showing no evidence of tumor at the time of measurement (Day 13). Furthermore, the maximally tolerated dose by both routes of administration was virtually the same, suggesting that Compound No. 1S has excellent bioavailability upon oral administration. In this experiment, tumors eventually grew at the site of implantation indicating either that ip treatment is optimal in this tumor model or that a longer duration of treatment is required for curative activity.

B16 Melanoma: This metastatic melanoma model has been widely used to evaluate and screen for antitumor drugs. When implanted sc, this tumor is refractory to most antitumor drugs. Compound No. 1S was evaluated in mice bearing sc B16 melanoma in three dose response studies. When given as a single dose on Days 1, 5 and 9, a maximally tolerated dose of Compound No. 1S administered ip or iv produced 99 percent tumor growth inhibition (TGI) with the majority of animals having no measurable tumors on Day 16 or 14 when control mice had tumors averaging 864 and 758 mm³ in the two experiments. When given on the optimal split dose treatment schedule described above, Compound No. 1S produced complete tumor growth inhibition over a broader dosage range. This is consistent with the results obtained in other tumor models. In the sc B16 melanoma model, tumors eventually grew in all treated animals and there were no cures. In this metastatic tumor model, however, there was a prolongation of lifespan which occurred with the complete inhibition of tumor growth. On the split-dose regimen there was 52 percent ILS while a single ip dose of 24 mg/kg on Days 1, 5, and 9 prolonged lifespan by 39 percent. On this latter schedule iv administration resulted in 53 percent ILS.

B16 Melanoma/F10 Subline: This subline of B16 melanoma, selected for increased metastatic properties was similar to the parent B16 melanoma in its responsiveness to Compound No. 1S. Treatment ip on Days 1, 5, 9 and 13 resulted in complete tumor growth inhibition at the maximally tolerated dose. Treatment iv on Days 1, 5 and 9 inhibited tumor growth by 97 percent at two dose levels. In these experiments, tumors were measured on Day 16 and tumors in control mice were very large, averaging 1927 and 1196 mm³. Tumors in all treated groups eventually grew and there were no cures. However, ip treatment at 25 kg resulted in 70 percent increase in lifespan (ILS); iv treatment at the same dose level gave 38 percent ILS.

ADJ PC$_6$ Plasmacytoma: This tumor model, which is most akin to the human cancer of multiple myeloma, was highly sensitive to Compound No 1S administered ip on Days 1, 5, 9 and 13. Tumors were measured on Day 19 and averaged 828 mm³ in volume in control mice. Compound No. 1S produced >90 percent inhibition of tumor growth at four dose levels at or below the maximally tolerated dose. There was 1 of 8 long term tumor-free survivors at each of the top three dose levels. As this tumor is not highly metastatic, median survival time was not determined.

M5076 Sarcoma: The M5076 sarcoma implanted sc was quite sensitive to Compound No. 1S with >90 percent TGI at three dose levels at or below a maximally tolerated dose. Tumors were measured on Day 17 when control tumors averaged 1045 mm$^3$. The drug was administered ip on Days 1, 5, 9 and 13. The drug was not curative in this model but prolonged lifespan by 31 percent.

Mammary Adenocarcinoma 16/C: This breast tumor model is a transplantable subline of the spontaneous mammary tumor of the C$_3$H mouse. Compound No. 15 inhibited tumor growth by 96 percent at the maximally tolerated dose of 10 mg/kg given ip on Days 1, 5, 9 and 13. Tumors were measured on Day 19 when the average tumor volume in control mice was 630 mm$^3$. In a second experiment on the same treatment schedule, Compound No. 1S produced 73 percent tumor growth inhibition (TGI) in mammary adenocarcinoma 16/C. As this tumor is not highly metastatic, animals were not held for survival.

Colon Adenocarcinoma 38: This nonmetastatic colon tumor model has been widely used in drug evaluation and is considered to be one of the more drug refractory tumor models. Compound No. 1S was administered ip as a single dose or on a split-dose regimen on Days 3, 10, 17 and 24. The more prolonged treatment regimen was chosen because of the slow growth of this solid tumor. Tumors were measured on Day 31 and averaged only 349 mm$^3$ in untreated controls. As in other tumor models, Compound No. 1S was more effective on the split-dose schedule producing >90 percent inhibition at two dose levels. Good activity (89 percent TGI) was evident on the single dose regimen as well.

Colon Adenocarcinoma 51: This is another slow growing colon tumor model which has proven to be refractory to most antitumor drugs. The protocol used for this tumor was similar to that of the colon adenocarcinoma 38. Compound No. 1S was active against colon adenocarcinoma 51 producing 88 percent TGI with a single dose regimen and 92 percent TGI on a split dose treatment. As in other tumors, Compound No. 1S was effective over a broader dosage range when given on the split dose regimen. Colon adenocarcinoma 51 was measured on Day 24 when control tumors averaged 766 mm$^3$.

Madison Lung Carcinoma: Madison lung carcinoma, like the Lewis lung carcinoma, is a rapidly growing undifferentiated tumor model with high metastatic activity. In contrast to the Lewis lung tumor, the Madison lung tumor is not highly sensitive to Compound No. 1S. On a single dose regimen given iv on Days 1, 5 and 9, there is virtually no tumor growth inhibition (28 percent TGI) at a maximally tolerated dose. On two additional experiments on the same treatment schedule with the drug given ip, Compound No. 1S produced only 50 percent and 23 percent TGI. However, on the optimal split-dose regimen Compound No. 1S, administered iv, did show activity against Madison lung carcinoma with 85 percent TGI at the maximally tolerated dose. The drug was somewhat less effective on this treatment schedule when given ip (74 percent TGI at the maximally tolerated dose). Madison lung tumors were measured on Day 12 or 13 in two separate experiments when tumors in control mice averaged 1571 and 942 mm$^3$, respectively, reflecting the rapid growth rate of this tumor. Thus, even in a refractory tumor the administration of Compound No. 1S on its optimal treatment regimen can result in significant tumor growth inhibition.

Colon Carcinoma 26: In this highly invasive and metastatic undifferentiated colon tumor, Compound No. 1S produced only marginal tumor growth inhibition (72 percent TGI) when given ip at its maximally tolerated dose on Days 1, 5, 9 and 13. Tumors were measured on Day 19 when control tumors averaged 1052 mm$^3$. It is unknown whether Compound No. 1S would demonstrate good activity in this tumor model if administered on its optimal split-dose regimen.

Multidrug Resistant Sublines

Although the most significant problem in cancer therapeutics is the inherent insensitivity of the common neoplasms to all of the available agents or combination regimens, another major problem is the emergence of resistant tumor cells from previously responsive tumors. The majority of patients with "chemosensitive" tumors such as nonsmall cell lung cancer, ovarian adenocarcinoma, acute nonlymphocytic leukemia, breast carcinoma and certain lymphomas can be placed into remission by combination regimens which have become established as front-line therapy for these diverse diseases. However, in most cases, patients present with recurrent disease and the ability to induce subsequent meaningful remission, even with highly intensive combination regimens, is greatly reduced. Characteristically, these recurrent tumors prove to be refractory to drugs which are structurally and/or mechanistically unrelated to the drugs which were initially employed to induce remission. This phenomenon of multidrug resistance is currently being intensively investigated in a number of laboratories. Recent evidence suggests that amplification and expression of the multidrug resistance (mdr) gene and presence of the mdr gene product. P170 membrane glycoprotein, is associated with multidrug resistance. P170 purportedly serves as an efflux transport pump with incredible diversity of substrate specificity. A recent paper suggests that strong expression of the mdr gene in certain previously untreated tumors such as pheochromocytoma and colon adenocarcinoma could be responsible at least in part for the inherent drug refractory phenotype of these tumors.

Thus, it is important to identify new agents which retain a high degree of activity against tumors which express the multidrug resistance phenotype. Such agents might hold promise for further advances in the treatment of chemosensitive tumors (i.e. by showing efficacy in previously treated patients or by killing the mdr subpopulation as a component of front line combination regimens) as well as for currently nonresponsive tumors which are insensitive to available drugs because of inate expression of the mdr gene. Camptothecin has proved to be unusual in that it is one of the few natural product cytotoxic agents that has not demonstrated cross-resistance in the well-characterized tumor sublines which show the mdr phenotype, i.e. P388 sublines resistant to doxorubicin, vincristine, amsacrine, ellipticine or mitoxantrone. Since most of the drugs which show cross-resistance in multidrug resistant cell lines are basic, it was expected that the addition of a basic side-chain to the camptothecin molecule, as in Compound No. 1S, would result in a compound which would be transported out of cells by P170 glycoprotein and thus prove ineffective in tumors expressing the mdr gene.

Compound No. 1S was evaluated in mice bearing P388 and its doxorubicin- and mitoxantrone-resistant sublines (Table 8). Doxorubicin and mitomycin c were included for comparison. P388/doxorubicin and P388/mitoxantrone retained sensitivity to Compound No. 1S. These multidrug resistant cell lines demonstrated the expected resistance to doxorubicin. P388/doxorubicin was also resistant to mitomycin c. Thus, Compound No. 1S retains the antitumor activity in multidrug resistant cell lines that is a characteristic of camptothecin.

Racemic Form of Compound No. 1

All of the biological studies described heretofore were carried out with the S isomer of Compound No. 1, i.e., the configuration at C-20 which exists in naturally-occurring camptothecin and 10-hydroxycamptothecin. A racemic form of Compound No. 1 was prepared by total synthesis and was evaluated for antitumor activity in mice bearing ip P388 leukemia (Table 9). The racemic form of Compound No. 1S, hereafter referred to as Compound No. 1RS, is highly active in P388 leukemia, producing 165 percent ILS with 1/6 long-term survivors at a dose of 29 mg/kg administered ip on Days 1 and 5. Although not quite as active as Compound No. 1S (cf Tables 5 and 8), Compound No. 1RS possesses excellent activity in this tumor model.

Different Salt Forms of Compound No. 1S

Compound No. 1S is water-soluble by virtue of the presence of the basic side-chain at position 9 which forms salts with acids such as acetic acid, hydrochloric acid and methanesulfonic acid. The experiments described in Tables 2 through 9 were performed with either the acetate or hydrochloride salts of Compound No. 1S. A soluble form of Compound No. 1S can also be prepared by basic hydrolysis of the E-ring lactone of Compound No. 1S with the formation of water-soluble alkali metal salts of the carboxylate form of the compound. A direct comparison of the acetate, hydrochloride, dihydrochloride and sodium salts of Compound No. 1S was carried out in mice bearing iv L1210 leukemia (Table 10). The compounds were administered as solutions in 5% dextrose iv on Days 1 and 5. The dihydrochloride salt was formed upon addition of excess hydrochloric acid and likely results from protonation of the quinoline nitrogen in Ring B, as well as the nitrogen of the dimethylaminomethyl group. Each salt form was active in this tumor model with 100 percent ILS evident for the acetate, 175 percent ILS for the hydrochloride, 133 percent ILS for the dihydrochloride, and 208 percent ILS for the sodium salt. The three acid salts were equipotent, i.e., they had identical maximally tolerated dose levels of 15 mg/kg. However, the sodium salt was about 3.5-fold less potent with a maximally tolerated dose of 54 mg/kg.

TABLE 3

Spectrum of Activity of Compound No. 1S in Animal Tumor Models

| Tumor Model | Activity at Maximally Tolerated Dose |
| --- | --- |
| ip Tumor Models | |
| P388 Leukemia | +++ |
| L1210 Leukemia | +++ |
| B16 Melanoma | ++ |
| B16 Melanoma/F10 Subline | ++ |
| M5076 Sarcoma | ++ |
| Colon Carcinoma 26 | − |
| iv Tumor Models | |
| P388 Leukemia | +++ |
| L1210 Leukemia | +++ |
| Lewis Lung Carcinoma | +++ |
| sc Tumor Models | |
| Lewis Lung Carcinoma | +++ |
| B16 Melanoma | ++ |
| B16 Melanoma/F10 Subline | ++ |
| ADJ-PC6 Plasmacytoma | ++ |
| M5076 Sarcoma | ++ |
| Mammary Adenocarcinoma 16/c | ++ |
| Colon Adenocarcinoma 38 | ++ |
| Colon Adenocarcinoma 51 | ++ |
| Madison Lung Carcinoma | + |
| Colon Carcinoma 26 | ± |

Compound No. 1S was administered ip or iv every fourth or seventh day for 2 to 4 courses beginning 1 to 3 days following tumor implantation.
+++ = curative (>200% increase in lifespan (ILS))
++ = >100% increase in lifespan (ILS) or >90% inhibition of tumor growth (TGI)
+ = >50% ILS or >70% TGI
− = <50% ILS or <70% TGI

TABLE 4

Comparison of Compound No. 1S with Camptothecin and 10-Hydroxycamptothecin in a Spectrum of Animal Tumor Models

| Tumor Model | Compound No. 1S | Camptothecin | 10-Hydroxycamptothecin |
| --- | --- | --- | --- |
| | Increase in Lifespan (ILS) or Inhibition of Tumor Growth (TGI) | | |
| ip Tumor Models | | | |
| P388 Leukemia | Curative | Curative | Curative |
| L1210 Leukemia | Curative | 172% ILS | 94% ILS |
| B16 Melanoma | 152% ILS | 36% ILS | 95% ILS |
| B16 Melanoma/F10 Subline | 105% ILS | 68% ILS | 100% ILS |
| M5076 Sarcoma | 105% ILS | 81% ILS | 98% ILS |
| Colon Carcinoma 26 | 25% ILS | 50% ILS | Curative |
| iv Tumor Models | | | |
| P388 Leukemia | Curative | 75% ILS | 40% ILS |
| L1210 Leukemia | Curative | 136% ILS | 100% ILS |
| Lewis Lung Carcinoma | Curative | not tested | not tested |
| sc Tumor Models | | | |
| Lewis Lung Carcinoma | Curative | 92% TGI | 4% TGI |
| B16 Melanoma | 100% TGI | 78% TGI | not tested |
| B16 Melanoma/F10 Subline | 100% TGI | 90% TGI | 58% TGI |
| ADJ-PC6 Plasmacytoma | 100% TGI | 100% TGI | 76% TGI |
| M5076 Sarcoma | 100% TGI | 100% TGI | 66% TGI |
| Mammary Adenocarcinoma 16/c | 96% TGI | 99% TGI | 61% TGI |
| Colon Adenocarcinoma 38 | 96% TGI | 100% TGI | not tested |
| Colon Adenocarcinoma 51 | 92% TGI | 75% TGI | not tested |
| Madison Lung Carcinoma | 85% TGI | 63% TGI | 33% TGI |

TABLE 4-continued

Comparison of Compound No. 1S with Camptothecin and 10-Hydroxycamptothecin in a Spectrum of Animal Tumor Models

| Tumor Model | Compound No. 1S | Camptothecin | 10-Hydroxycamptothecin |
|---|---|---|---|
| | Increase in Lifespan (ILS) or Inhibition of Tumor Growth (TGI) | | |
| Colon Carcinoma 26 | 72% TGI | 66% TGI | 37% TGI |

TABLE 5

Activity of Compound No. 1S in Mice Bearing ip implanted Tumors

| Tumor Model | Treatment Schedule/ Route of Administration | Dose (mg/kg/ injection) | ILS (%) | Long-Term Survivors |
|---|---|---|---|---|
| P388 Leukemia | A/ip | 30 | toxic | |
| | | 15 | >200 | 4/6 |
| | | 7.5 | 125 | |
| | | 3.8 | 92 | |
| L1210 Leukemia | A/ip | 25 | toxic | |
| | | 15 | 219 | 2/6 |
| | | 9 | 138 | |
| | | 5.4 | 81 | |
| | | 3.2 | 31 | |
| B16 Melanoma | B/ip | 25 | toxic | |
| | | 15 | 152 | |
| | | 9 | 100 | |
| | | 5.4 | 52 | |
| | | 3.2 | 43 | |
| B16 Melanoma/ F10 Subline | B/ip | 25 | toxic | |
| | | 15 | 105 | |
| | | 9 | 68 | |
| | | 5.4 | 63 | |
| | | 3.2 | 37 | |
| M5076 Sarcoma | C/ip | 10 | toxic | |
| | | 5 | toxic | |
| | | 2.5 | 105 | |
| | | 1.2 | 75 | 1/8 |
| | | 0.62 | 70 | 1/8 |
| M5076 Sarcoma | C/sc | 10 | toxic | |
| | | 5 | toxic | |
| | | 2.5 | 98 | |
| | | 1.2 | 70 | 1/8 |
| | | 0.62 | 36 | |
| Colon Carcinoma 26 | B/ip | 40 | toxic | |
| | | 20 | toxic | |
| | | 10 | 25 | |
| | | 5 | 5 | |
| | | 2.5 | 7 | |

TABLE 6

Activity of Compound No. 1S in Mice Bearing iv-implanted Tumor

| Tumor Model | Treatment Schedule/ Route of Administration | Dose (mg/kg/ injection) | ILS (%) | Long-Term Survivors |
|---|---|---|---|---|
| P388 Leukemia | A/ip | 25 | 279 | 2/6 |
| | | 15 | 132 | |
| | | 9 | 100 | |
| | | 5.4 | 58 | |
| | | 3.2 | 42 | |
| P388 Leukemia | A/iv | 25 | toxic | |
| | | 19 | 250 | 2/6 |
| | | 14 | 145 | |
| | | 10 | 110 | |
| | | 7.9 | 65 | |
| L1210 Leukemia | A/ip | 25 | toxic | |
| | | 15 | 171 | 1/6 |
| | | 9 | 136 | |
| | | 5.4 | 93 | |
| | | 3.2 | 57 | |
| L1210 Leukemia | D/iv | 40 | toxic | |
| | | 24 | >300 | 4/7 |
| | | 14 | 157 | |
| | | 8.6 | 129 | |
| | | 5.2 | 71 | |

TABLE 6-continued

Activity of Compound No. 1S in Mice Bearing iv-implanted Tumor

| Tumor Model | Treatment Schedule/ Route of Administration | Dose (mg/kg/ injection) | ILS (%) | Long-Term Survivors |
|---|---|---|---|---|
| L1210 Leukemia | E/iv | 6 | toxic | |
| | | 3.6 | >300 | 5/7 |
| | | 2.2 | >300 | 1/7 |
| | | 1.3 | 243 | 2/7 |
| | | 0.78 | 186 | |
| Lewis Lung Carcinoma | B/ip | 25 | toxic | |
| | | 15 | >200 | 7/7 |
| | | 9 | 111 | 1/7 |
| | | 5.4 | 37 | |
| | | 3.2 | 16 | |

TABLE 7

Activity of Compound No. 1S in Mice Bearing sc-implanted Tumors

| Tumor Model | Treatment Schedule/ Route of Administration | Dose (mg/kg/ injection) | TGI (%) | Mice without Palpable Tumors |
|---|---|---|---|---|
| Lewis Lung Carcinoma | B/ip | 25 | toxic | |
| | | 15 | 100 | 8/8* |
| | | 9 | 99 | 7/8** |
| | | 5.4 | 68 | 2/8 |
| | | 3.2 | 31 | |
| Lewis Lung Carcinoma | F/iv | 25 | 99 | 5/8 |
| | | 15 | 95 | 3/8 |
| | | 9 | 93 | 1/8 |
| | | 5.4 | 87 | 4/8 |
| Lewis Lung Carcinoma | F/po | 45 | toxic | |
| | | 27 | 99 | 4/8 |
| | | 16 | 90 | 1/8 |
| | | 9.7 | 89 | 2/8 |
| | | 5.8 | 51 | |
| B16 Melanoma | F/ip | 24 | 99 | 7/8 |
| | | 14 | 57 | 3/8 |
| | | 8.6 | 63 | 3/8 |
| | | 5.2 | 20 | 1/8 |
| | | 3.1 | 63 | 2/8 |
| B16 Melanoma | F/iv | 25 | toxic | |
| | | 15 | 99 | 7/8 |
| | | 9 | 96 | 6/8 |
| | | 5.4 | 79 | 3/8 |
| | | 3.2 | 54 | 2/8 |
| B16 Melanoma | C/ip | 6 | 100 | 7/7 |
| | | 3.6 | 100 | 7/7 |
| | | 2.2 | 92 | 2/8 |
| | | 1.3 | 64 | 1/8 |
| | | 0.78 | 46 | 1/8 |
| B16 Melanoma/ F10 Subline | B/ip | 25 | 100 | 7/8 |
| | | 15 | 87 | |
| | | 9 | 57 | |
| | | 5.4 | 62 | |
| | | 3.2 | 52 | |
| B16 Melanoma/ F10 Subline | F/iv | 25 | 97 | 6/8 |
| | | 15 | 97 | 7/8 |
| | | 9 | 60 | 2/8 |
| | | 5.4 | 34 | 1/8 |
| | | 3.2 | 22 | 1/8 |
| ADJ-PC6 Plasmacytoma | B/ip | 25 | toxic | |
| | | 15 | 100 | 7/7*** |
| | | 9 | 100 | 8/8*** |
| | | 5.4 | 92 | 4/8*** |
| | | 3.2 | 93 | 3/8 |
| M5076 Sarcoma | B/ip | 25 | toxic | |
| | | 15 | 100 | 8/8 |
| | | 9 | 98 | 6/8 |
| | | 5.4 | 92 | 3/8 |
| | | 3.2 | 64 | 2/8 |
| Mammary Adenocarcinoma 16/C | B/ip | 20 | toxic | |
| | | 10 | 96 | 3/8 |
| | | 5 | 61 | 2/8 |
| | | 2.5 | 59 | 1/8 |
| Colon Adenocarcinoma 38 | G/ip | 24 | 89 | 4/7 |
| | | 14 | 78 | 5/8 |

TABLE 7-continued

Activity of Compound No. 1S in Mice Bearing sc-implanted Tumors

| Tumor Model | Treatment Schedule/ Route of Administration | Dose (mg/kg/ injection) | TGI (%) | Mice without Palpable Tumors |
|---|---|---|---|---|
| | | 8.6 | 55 | 3/7 |
| | | 5.2 | 0 | 1/7 |
| | | 3.1 | 0 | 2/7 |
| Colon Adenocarcinoma 38 | H/ip | 6 | 96 | 5/7 |
| | | 3.6 | 93 | 6/7 |
| | | 2.2 | 74 | 4/7 |
| | | 1.3 | 68 | 4/7 |
| | | 0.78 | 53 | 2/7 |
| Colon Adenocarcinoma 51 | G/ip | 24 | 88 | 3/8 |
| | | 14 | 76 | 1/8 |
| | | 8.6 | 53 | 1/8 |
| | | 5.2 | 36 | |
| | | 3.1 | 34 | |
| Colon Adenocarcinoma 51 | H/ip | 3.6 | 92 | 4/8 |
| | | 2.2 | 89 | 4/8 |
| | | 1.3 | 88 | 3/8 |
| | | 0.78 | 73 | 1/8 |
| | | 0.47 | 37 | |
| Madison Lung Carcinoma | F/iv | 24 | 28 | 1/8 |
| | | 12 | 0 | |
| | | 6 | 21 | |
| | | 3 | 0 | |
| | | 1.5 | 0 | |
| Madison Lung Carcinoma | C/iv | 3 | toxic | |
| | | 1.5 | 85 | 3/8 |
| | | 0.75 | 63 | 1/8 |
| | | 0.38 | 41 | |
| | | 0.19 | 0 | |
| Colon Carcinoma 26 | B/ip | 20 | toxic | |
| | | 10 | 72 | |
| | | 5 | 39 | |
| | | 2.5 | 38 | |

*4/8 long-term, tumor-free survivors
**2/8 long-term, tumor-free survivors
***⅛ long-term, tumor-free survivors Treatment schedules are: B=Days 1, 5, 9 and 13; C=every 3 hours×4 on Days 1, 5 and 9; F=Days 1, 5 and 9; G=Days 3, 10, 17 and 24; H=every 3 hours×4 on Days 3, 10, 14 and 24

Inhibition of tumor growth (TGI) is based on mean tumor volume of groups of 7 or 8 mice relative to untreated controls. Tumors were measured between Days 12 and 19 (except Day 24 for Colon 51 and Day 31 for Colon 38). In all but two experiments, all untreated control mice (21 or 24 mice/group) had measurable tumors. In B16/F10, Schedule F, 21/24 control mice had measurable tumors. In the experiment with Colon adenocarcinoma 38, 19/21 control mice had measurable tumors.

TABLE 8

Lack of Cross-Resistance to Compound No. 1S of Multidrug Resistant Sublines of P388 Leukemia

| Compound | Dose (mg/kg, ip, Days 1 and 5) | P388 ILS (%) | P388 NCK (log) | P388/Doxorubicin ILS (%) | P388/Doxorubicin NCK (log) | P388/Mitoxantrone ILS (%) | P388/Mitoxantrone NCK (log) |
|---|---|---|---|---|---|---|---|
| Compound No. 1S | 25 | toxic | | toxic | | toxic | |
| | 15 | 228 | 6.5 | 176 | 6.0 | 107 | 5.7 |
| | 9 | 211 | 6.5 | 90 | 2.2 | 79 | 3.6 |
| | 5.4 | 128 | 3.5 | 33 | 0 | 57 | 2.1 |
| | 3.2 | 67 | 1.0 | 14 | 0 | 29 | 0 |
| Doxorubicin | 9 | 233 | 6.5 | 14 | 0 | 7 | 0 |
| | 5.4 | 156 | 4.6 | 19 | 0 | 4 | 0 |
| | 3.2 | 172 | 5.3 | 24 | 0 | 0 | 0 |
| | 1.9 | 167 | 5.1 | 24 | 0 | 0 | 0 |
| | 1.2 | 117 | 3.0 | 19 | 0 | 0 | 0 |
| Mitomycin C | 7.5 | 178 | 5.5 | 52 | 0.5 | 104 | 5.5 |
| | 4.5 | 156 | 4.6 | 62 | 1.0 | 136 | 6.5 |
| | 2.7 | 128 | 3.5 | 52 | 0.5 | 54 | 1.8 |
| | 1.6 | 106 | 2.6 | 48 | 0.3 | 29 | 0 |
| | 1.0 | 83 | 1.7 | 29 | 0 | 14 | 0 |

Increase in lifespan (ILS) is based on median survival time of groups of 6 mice. Net tumor cell kill (NCK) is calculated from median survival time by standard methods, since survival time is a linear function of the log tumor cell burden. As the mitoxantrone-resistant subline has a longer doubling time than the other two cell lines used in this experiment, a smaller ILS is associated with greater NCK than in P388 or doxorubicin-resistant cell line.

TABLE 9

Activity of Racemic Mixture of Compound No. 1S in Mice Bearing ip P388 Leukemia

| Compound No. | Dose (mg/kq, ip, Days 1 & 5) | ILS (%) | Long-term Survivors |
|---|---|---|---|
| 1RS | 29 | 165 | 1/6 |
|  | 14 | 135 |  |
|  | 7.2 | 80 |  |
|  | 3.6 | 30 |  |

Animals were implanted ip with $10^6$ cells. Increase in lifespan (ILS) is based on median survival time of groups of 6 mice relative to untreated controls. Long-term survivors were tumor-free on Day 45.

TABLE 10

Comparative Activity of Different Salt Forms of Compound No. 1S in Mice Bearing iv L1210 Leukemia

| Compound | Dose (mg/kq, ip, Days 1 & 5) | ILS (%) |
|---|---|---|
| 1S (acetate salt) | 25 | toxic |
|  | 15 | 100 |
|  | 9 | 83 |
|  | 5.4 | 67 |
|  | 3.2 | 50 |
| 1S (hydrochloride salt) | 25 | toxic |
|  | 15 | 175 |
|  | 9 | 125 |
|  | 5.4 | 92 |
|  | 3.2 | 50 |
| 1S (dihydrochloride salt) | 25 | toxic |
|  | 15 | 133 |
|  | 9 | 83 |
|  | 5.4 | 50 |
|  | 3.2 | 50 |
| 1S (sodium salt) | 90 | toxic |
|  | 54 | 208 |
|  | 32 | 133 |
|  | 19 | 100 |
|  | 12 | 67 |
|  | 6.5 | 33 |

Animals were inoculated iv with $10^6$ cells. Increase in lifespan (ILS) is based on median survival time of groups of 6 mice relative to untreated controls.

Pharmaceutical Composition and Method of Treatment

The pharmaceutical compositions of this invention comprise an effective tumor cell growth-inhibiting amount of a compound of Formula (I) and an inert pharmaceutically acceptable carrier or diluent. These compositions are prepared in dosage unit form appropriate for parenteral or oral administration.

A compound of Formula (I) is administered in conventional dosage form prepared by combining a therapeutically effective amount (i.e., an effective tumor growth inhibiting amount) of a compound of Formula (I) ("active ingredient") with standard pharmaceutical carriers or diluents according to conventional procedures. These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax, ethylcellulose, hydroxypropylmethylcellulose, methylmethacrylate and the like.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dose form, a pharmaceutically acceptable salt of a compound of Formula (I) is dissolved in an aqueous solution of an organic or inorganic acid, such as 0.3 M solution of succinic acid, or, preferably, citric acid. If a soluble salt form is not available, the compound of Formula (I) is dissolved in a suitable cosolvent or combinations thereof. Examples of such suitable cosolvents include, but are not limited to, alcohol, propylene glycol, polyethylene glycol 300, polysorbate 80, glycerin and the like in concentrations ranging from 0-60% of the total volume.

The composition may also be in the form of a solution of a salt form of the active ingredient in an appropriate aqueous vehicle such as water or isotonic saline or dextrose solutions. For those Formula (I) compounds which do not have a basic side-chain in the 9-position such as Compounds No. 2S and 10S (see Table 2 for structure), an alkali metal salt of the carboxylate formed on alkaline hydrolysis of the E-ring lactone would yield a soluble salt as exemplified by the sodium salt of Compound No. 1S.

It will be appreciated that the actual preferred dosages of the Formula (I) compounds used in the compositions of this invention will vary according to the particular complex being used, the particular composition formulated, the mode of administration and the particular site, host and disease being treated. Optimal dosages for a given set of conditions can be ascertained by those skilled in the art using conventional dosage determination tests in view of the above experimental data. For parenteral administration, the dose generally employed is from about 20 to about 150 mg/m$^2$ of body surface area per day for one to five days, preferably repeated about every fourth week for four courses of treatment. For oral administration, the dose generally employed is from about 20 to about 150 mg/m$^2$ of body surface area per day for one to five days, with courses of treatment repeated at appropriate intervals.

The method for inhibiting the growth of animal tumor cells sensitive to a compound of Formula (I) in accordance with this invention comprises administering to a host animal afflicted with said tumor cells an effective tumor growth-inhibiting amount of a compound of Formula (I). As described above, during the course of treatment the active ingredient will be administered parenterally or orally on a daily basis in an amount selected from about 20 mg/m$^2$ to about 150 mg/m$^2$ of body surface area for one to five days, with courses of treatment repeated at appropriate intervals.

The following Examples illustrate (a) the protocol used for assessing the activity of various compounds of Formula (I) in transplanted murine tumor models, (b) the chemical preparation of the Formula (I) compounds used in the compositions and methods of this invention, and (c) an oral and a parenteral pharmaceutical composition of this invention.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLES

I. Protocols Used For Transplanted Murine Tumor Models

The protocols utilized for the evaluation of the antitumor activity of Formula (I) compounds are well established and widely utilized by those skilled in the art of assessing the activity of drugs in preclinical tumor models. These studies generally follow the protocols established by the National Cancer Institute as described by Geran et al., Cancer Chemotherapy Reports, Part 3, Vol. 3, 1-103, 1972.

(A) ip Tumor Models

Tumors used in these studies—P388 leukemia and its doxorbicin—and mitoxanrone-resistant sublines, L1210 leukemia, B16 melanoma, B16 melanoma/F10 subline, M5076 sarcoma and colon carcinoma 26—are maintained by serial transplantation in syngeneic strains of mice. For the leukemias, these tumors are maintained in DBA/2 mice. The M5076 sarcoma, the B16 melanoma and its F10 subline are maintained in C57B1/6 mice and the colon sarcinoma 26 is maintained in BALB/c mice. The leukemias and the M5076 sarcoma are serially transplanted i.p. as ascites cell suspensions while the B16 melanoma lines and the colon carcinoma 26 are serially transplanted as s.c. solid tumors.

For therapeutic trials, tumors are aseptically removed from donor mice and prepared as suspensions for implantation ip into test animals. The test animals for the colon carcinoma 26 are female BALB/c mice (20-25 gm). The test animals for the other tumor models are syngeneic female $F_1$ hybrid $B6D2F_1$ mice (C57B1/6 x DBA/2). The inoculum level varies with the type of tumor: P388 leukemia is inoculated at $10^6$ cells per mouse, L1210 leukemia at $10^5$ or $10^6$ cells per mouse, M5076 sarcoma at $5 \times 10^6$ cells per mouse. For implantation of the B16 melanoma lines and the colon carcinoma 26, s.c. tumors from donor mice are minced and homogenized in loose fitting teflon glass homogenizer to give a tumor brei. The inoculum levels are 0.5 ml of a 10 percent (w:v) brei of the B16 melanoma lines and 0.5 ml of a 5 percent (w:v) brei of colon carcinoma 26. After tumor inoculation, mice randomized to treatment groups comprised of 6-8 mice each. In each experiment, there are three groups of untreated control mice. Drugs are dissolved or suspended in appropriate aqueous vehicles and given by a variety of routes and schedules of administration over a range of dose levels. Animals are housed in shoebox cages and are monitored daily for mortality for 30 (L1210), 45 (P388) or 60 (B16, M5076, colon 26) days. The endpoint for activity is median survival time and increase in lifespan relative to untreated controls. A drug is considered active in these tumor models if it prolongs lifespan by $\geq 40$ percent.

B. iv Tumor Models

Tumors used in these studies P388 leukemia, L1210 leukemia and Lewis lung carcinoma—are maintained by serial transplantation in syngeneic strains of mice, DBA/2 for the leukemias and C57B1/6 for Lewis lung carcinoma. The leukemias are serially transplanted i.p. as ascites cell suspensions while the Lewis lung carcinoma is serially transplanted as a s.c. solid tumor.

For therapeutic trials, tumors were aseptically removed from donor mice and prepared as suspensions for implantation into test animals which for each tumor are syngeneic female $F_1$ hybrid $B6D2F_1$ mice (C57B1/6×DBA/2). The inoculum level varies with the type of tumor: P388 leukemia is inoculated at $10^6$ cells per mouse, L1210 leukemia at $10^5$ or $10^6$ cells per mouse, and Lewis lung carcinoma at 0.25 ml of a 10 percent (w:v) brei. The brei of Lewis lung carcinoma is prepared as described above for B16 melanoma. After tumor inoculation, mice are randomized to treatment groups of 6 to 8 mice each. In each experiment, there are three groups of untreated control mice.

Drugs are dissolved or suspended in appropriate aqueous vehicles and given i.p. or i.v. on various treatment schedules over a range of dosage levels. Animals are housed in shoebox cages and monitored daily for mortality for 30 (L1210), 45 (P388) or 60 (Lewis lung) days. The endpoint for activity is median survival time and increase in lifespan relative to untreated controls. A drug is considered active in these tumor models if it prolongs lifespan by $\geq 40$ percent.

C. s.c. Tumor Models

Tumors used in these studies are maintained by serial transplantation in syngeneic strains of mice C57BL/6 for Lewis lung carcinoma, B16 melanoma and its F10 subline, M5076 sarcoma and colon adenocarcinoma 38; BALB/c for colon carcinoma 26, ADJ-PC6 plasmacytoma Madison lung carcinoma and colon adenocarcinoma 51, C3H for mammary adenocarcinoma 16/c. With the exception of the M5076 sarcoma, which is maintained as a i.p ascites cell suspension, all of the tumors were serially transplanted as s.c. solid tumors.

For therapeutic trials, tumors were aseptically removed from donor mice and prepared for implantation s.c. into test animals. The test animals for Lewis lung carcinoma, B16 melanoma and its F10 subline, M5076 sarcoma and colon adenocarcinoma 38 are syngeneic female $F_1$ hybrid B6D2F mice (C57B1/6×DBA/2). ADJ-PC6 plasmacytoma and colon carcinoma 26 are evaluated in female BALB/c mice. Madison lung carcinoma and colon adenocarcinoma 51 are evaluated in syngeneic female $F_1$ hybrid $CD2F_1$ mice (BALB/c×-DBA/2). Mammary adenocarcinoma 16/c is evaluated in female C3H mice. The inoculum varies with the tumor. Colon adenocarcinomas 38 is implanted as 2 mm fragments by trochar. M5076 sarcoma and ADJ-PC6 plasmacytoma are implanted as cell suspensions at $5 \times 10^6$ and $2 \times 10^6$ cells per mouse, respectively. Colon carcinoma 26, colon adenocarcinoma 51, Lewis lung carcinoma, Madison lung carcinoma and B16 melanoma and its F10 subline are implanted as tumor breis prepared as described above in a volume of 0.5 ml. The brei concentration was 10 percent (w:v) except for colon carcinoma 26 for which the brei concentration was 5 percent (w:v). After tumor inoculation, mice are randomized to treatment groups of 7 or 8 mice. In each experiment, there are three groups of untreated control mice.

Drugs are dissolved or suspended in appropriate aqueous vehicles and given by a variety of routes of administration and treatment schedules over a range of dosage levels. Animals are housed in shoebox cages and are monitored daily for mortality. At a time when untreated control animals have large measurable tumors (generally >500 mm³) tumors in all animals are measured in perpendicular diameters with a vernier caliper and tumor volume is calculated by the formula: length×(width)²×0.5. Time for tumor measurement is dependent on the different rates of tumor growth of the different tumors: the most rapidly growing tumors such as the Lewis and Madison lung tumors, B16 melanoma and its F10 subline were measured between Days 12 and 16. The slower growing tumors were measured at later time points—17 days for M5076 sarcoma, 16 or 19 days for mammary adenocarcinoma 16/c, 19 days for ADJ-PC6 plasmacytoma and colon carcinoma 26, 24 days for colon adenocarcinoma 51, and 31 days for colon adenocarcinoma 38. The endpoints for activity are mean tumor volume, percent tumor growth inhibition relative to untreated controls and the number of animals without palpable tumors on the day of measurement. A drug is considered active in these tumor models if it produces ≧70 percent inhibition of tumor growth at or below a maximally tolerated dose.

For highly metastatic tumors including: Lewis and Madison lung tumors, colon carcinoma 26 and B16 melanoma and its F10 subline, tumor-bearing mice are monitored for survival time as well. For the less metastatic tumor models, tumor-bearing mice are killed following tumor measurement. In this setting, an increase in lifespan of ≧30 percent is considered to be evidence of drug activity.

II. Synthesis of Compounds of Formula (I)

In the following synthetic examples, temperature is in degrees Centigrade (°C.). Unless otherwise indicated, all of the starting materials were obtained from commercial sources.

EXAMPLE 1

Preparation of (20 S) 1,2,6,7-tetrahydrocamptothecin

Camptothecin (32.0 g, 0.092 mol.) obtained from Tainjain-SK&F Ltd., Tainjain, China, was combined with Pt⁰ [prepared by pre reduction of 8.0 g. amorphous PtO₂ in 800 mL HOAc for 1.5 hour (h) under 1 atmosphere (atm.) H₂] and HOAc (1.6 L). Reduction was carried out at 1 atm. H₂ for 8.5 h. while vigorously stirring the mixture. At the end of this time, the theoretical amount of H₂ had been absorbed (slightly more than 4.1 L) and the uptake of H₂ had slowed considerably. The reaction was degassed with a stream of Ar for approximately 10 minutes (min.), and then filtered through a celite pad which was washed with HOAc (200 mL).

The resulting solution was used immediately in the following reaction described in Example 2.

EXAMPLE 2

Preparation of (20 S) 10-Hydroxycamptothecin

To the vigorously stirred solution of 1,2,6,7-tetrahydrocamptothecin, prepared as described above in Example 1, was added Pb(OAc)₄ (64 g., 0.144 mol.) in one portion. The reaction was stirred under Ar for 30 min., and all of the Pb(OAc)₄ had dissolved. Concentration gave a gummy residue which was triturated with ice cold H₂O (1 L) to give a light brown solid which was filtered off, washed with additional ice cold H₂O (200 mL), pressed dry with a rubber dam and air dried overnight. The resulting partially wet product contained 44.3% 10-Hydroxycamptothecin, 26.9%, 10-Acetoxycamptothecin, and 23.1% Camptothecin based on high pressure liquid chromatography (HPLC) analysis (Whatman Partisil 5 ODS3 Rac II 60% CH₃OH/H₂O).

The crude mixture was combined with 1.7 L 50% aqueous HOAc and refluxed overnight. The reaction was cooled and concentrated to approximately 50 100 mL. Ice cold H₂O (1 L) was added and the precipitate was filtered off, washed with additional ice cold H₂O (200 mL), pressed dry with a rubber dam, and dried under high vacuum for 2 days to give 21.16 g. of material which contained 70.9% 10-Hydroxycamptothecin, 1.2% 10-Acetoxycamptothecin, and 21.3% Camptothecin based on HPLC analysis.

EXAMPLE 3

Preparation of (20 S) 9-Dimethylaminomethyl-10-hydroxycamptothecin Acetate Salt

10-Hydroxycamptothecin (20 g which assayed at 62% 10-Hydroxycamptothecin and therefore contained 12.4 g, 34.1 mmol of 10-Hydroxycamptothecin), prepared as described in Example 2, was combined with HOAc (620 mL), 37% aqueous CH₂O (12.4 mL, approximately 149 mmol) and 40% aqueous dimethylamine (12.4 mL, approximately 109 mmol) and stirred for approximately 18 h and the thin layer chromatography (tlc) indicated some remaining starting material (tlc in 9:1 CH₂Cl₂, CH₃OH on silica gel). This system is suitable for following the disappearance of 10-hydroxycamptothecin but not for monitoring the formation of product. Additional 37% aqueous CH₂O (6 ml, approximately 72 mmol), and 40% aqueous dimethylamine (6 mL, approximately 53 mmol) was added and stirring was continued for an additional 24 h. The reaction was concentrated to dryness, triturated with 0.5% aqueous HOAc (1 L), filtered and the solid was washed with additional 0.5% aqueous HOAc (500 mL). The dried solid weighed 6.3 g and was 94% recovered camptothecin by HPLC (Whatman Partisil 10 ODS 3 50% CH₃OH/H₂O, retention time 9 min.). The combined aqueous filtrates were extracted with EtOAc (3×600 mL), and petroleum ether (600 mL) and then lyophilized.

Chromatography of the crude residue was achieved by injection of the material in solvent A (solvent A=99% H₂O, 1% HOAc) (600 mL) and elution at 350 mL/min. through a 50 mm×600 mm steel column packed with 680 g Whatman Partisil 40 ODS 3 with a 34 min linear gradient from 100% solvent A to 40% solvent B (solvent B=99% CH₃OH, 1% HOAc). The chromatography was monitored at 410 nm and 1 L fractions were collected and those which assayed at ≧99% pure by analytical HPLC (Whatman Partisil 10 ODS 3 50% CH₃OH/H₂O, retention time 9 min.) were pooled, concentrated and redissolved in a minimum of 0.5% aqueous HOAc and lyophilized to give 10.58 g (62%) of the named product.

IR (KBr) 3400, 2960, 1740, 1650, 1590 cm⁻¹. ¹H NMR (CDCl₃/CD₃OD) 1.04 (t,3,J=7Hz,C18), 1.96(q,2,J=7Hz,C19), 2.01(s,3,$\underline{CH_3}CO_2$) 2.50(s,6,$(\underline{CH_3})_2$NH), 4.20(s,2,Ar$\underline{CH_2}$N), 5.28 (d,1,J=19Hz,C17), 5.29(s,2,C5), 5.50(d,1,J=19Hz,C17), 7.42(d,J=9Hz,C11), 7.67(s,1,C14), 8.05(d,J=9Hz,C12), 8.51(s,C7). Calcd for C₂₃H₂₃N₃O₅ 1 HOAc 1 H₂O (mw=515.5): C,58.24;

H,5.67; N,8.15. Fd: C,58.55; H$_{5.22}$; N,8.54. Pb analysis<14.5 ppm.

Additional named product material which was >90% pure by HPLC (see, above) was concentrated to dryness and later rechromatographed with similar material isolated from other runs.

EXAMPLE 4

Preparation of (20 S) 9-Morpholinomethyl-10-hydroxycamptothecin Acetate Salt 10-Hydroxycamptothecin (100 mg, 0.27 mmol), prepared as described in Example 2, 37% aqueous $CH_2O$ (0.5 mL), morpholine (0.1 mL) and 2:1 HOAc/EtOH (10 mL) were combined and stirred overnight. 10-Hydroxycamptothecin had reacted (tlc, silica gel, 9:1 $CH_2Cl_2/CH_3OH$) and the reaction was concentrated to dryness, dissolved in ca. 5 mL $H_2O$ containing several drops of HOAc and the insoluble material was filtered off. The filtrate was lyophilized and the lyophilizate was chromatographed (15 mm×250 mm silica medium pressure liquid chromatography (MPLC), eluting with $CH_2Cl_2$ containing 0–2% $CH_3OH$) to give a residue which was dissolved in dilute aqueous HOAc and lyophilized to give 53 mg (38%) of the title compound. IR (KBr) 3400, 3100, 2960, 2920, 2840, 1740, 1650, 1590 cm$^{-1}$ H NMR ($CDCl_3/CD_3OD$) δ1.12 (t,3,J=7Hz,C18), 1.94 (q,2,J=7Hz,C19), 2.73(m,4,morpholino-$CH_2N$), 3.83 (m,4,morpholino-$CH_2O$) 4.19 (s,2,ArCH$_2$N), 5.26(s,2,C5), 5.25(d,1,J=16Hz, C17), 576(d1,J=16Hz,C17), 7.27(s,1,C14), 7.40(d,1,J=8Hz,CII), 8.07(d1,J=8Hz,C12), 8.36(s,1,C7). Calcd. for $CH_{25}H_{25}N_3O_6$ $CH_3$ $CO_2H$ (mw=525.6): C,61.71; H,5.95; N,8.00. Fd.: C,61.30; H,5.44; N,8.35.

EXAMPLE 5

Preparation of (20 S) 9-N-Methylpiperazinylmethyl-10-hydroxycamptothecin Acetate Salt 10-Hydroxycamptothecin (100 mg, 0.27 mmol), prepared as described in Example 2, 2:1 HOAc/EtOH (10 mL), 37% aq. $CH_2O$ (0.5 mL) and N-Methylpiperazine (0.1 mL) were combined and stirred for 20 hr. 10-Hydroxycamptothecin had reacted (tlc 9:1 $CH_2Cl_2/CH_3OH$) and the reaction was concentrated, dissolved in $H_2O$ (50 mL) and washed with EtOAc (5×20 mL) and petroleum ether (20 mL) and the aqueous phase was lyophilized. The residue was redissolved in dilute aq. HOAc and chromatoqraphed on MPLC (Whatman Partisil 40 ODS3, 9 mm×250 column) eluting with 0–20% $CH_3OH$ in $H_2O$ containing 0.02% HOAc. The desired lyophilized to give 67 mg (46%) of the title compound. IR (KBr) 3400, 2960, 2910, 1740, 1650, 1590 cm$^{-1}$. $^1$H NMR ($CDCl_3/CD_3OD$) δ1.03(t,3,J=7Hz,C18), 1.89(q,2,J=7Hz), 2.02(s,>3,$CH_3CO_2H$), 2.37(s,3, NCH$_3$), 2.65(m,8,piperazino-$CH_2$), 4.21(s,2,ArCH$_2$), 5.26(s,2,C5), 5.30(d,1,J=16Hz,C17), 5.71(d,1,J=16Hz,C17), 7.45(d,1,J=7Hz,C11), 8.05(d,1,J=7Hz,C12), 8.47(s,1,C7). Calcd. for $C_{26}H_{28}N_4O_5$ 1½ HOAc ¼ $H_2O$ (mw=528.1); C,61.41; H,6.01, N,10.61. Fd: C,61.62; H,5.74; N,10.93.

EXAMPLE 6

Preparation of (20 S) 9-(4'-Piperidinopiperidinyl) methyl-10-hydroxycamptothecin Acetate Salt 10-Hydroxycamptothecin (100 mg, 0.27 mmol), prepared as described in Example 2, 4-piperidinopiperidine (100 mg, 0.60 mmol), 37% aqueous $CH_2O$ (0.5 mL) and 2:1 HOAc/EtOH (10 mL) were stirred for 20 hr. The 10-Hydroxycamptothecin had reacted (tlc, silica gel, 9:1 $CH_2Cl_2/CH_3OH$) and the reaction was concentrated, dissolved in 1% aqueous acetic acid, filtered, and lyophilized. MPLC (Whatman Partisil 40 ODS3, 9×250 mm column) eluting with $H_2O$ (100 mL) and then 0–80% $CH_3OH$ in 0.02% aqueous HOAc gave 44 mg (30%) of the title compound after lyophilization. IR (KBr) 3400, 2940, 1745, 1660, 1590 cm$^{-1}$. $^1$H NMR (CDCl OD) δ0.99 (t,3,J=7Hz,C18), 1.3–3.3 (m,19, piperidine, C19), 4.11 (s,2,CH$_2$N), 5.21 (s,2,C5), 5.25 (d,1,J=16Hz, C17), 5.70 (d,1,J=16Hz,C17), 7.85 (d,1.J=7Hz,C11), 7.59 (s,1,C14), 8.00 (d,1,J=7Hz,C12), 8.35 (s,1,C7). Calcd. for $C_{31}H_{36}N_4O_5$ 1½ $H_2O$ (mw=631.7):C,58.94; H,6.22; N,8.81. Fd. C,59.02; H,6.44; N,8.53.

EXAMPLE 7

Preparation of (20 S) 9-(2'-Hydroxyethylamino) methyl-10-hydroxycamptothecin Acetate Salt 10-Hydroxycamptothecin (200 mg, 0.55 mmol), prepared as described in Example 2, paraformaldhyde (16 mg, 0.55 mmol). ethanolamine (61 mg, 1.1 mmol), and HOAc (6 mL) were stirred for 48 hr after which most of the 10-Hydroxycamptothecin had reacted. The reaction was concentrated, redissolved in dilute HOAc (200 mL) and washed with EtOAC (4×30 mL) and petroleum ether (30 mL) and the resulting aq. soln was lyophilized. The crude lyophilizate was dissolved in $H_2O$ (50 mL). MPLC (Whatman Partisil 40 ODS3, 15 mm×250 mm column) eluting with $H_2O$ (100 mL) followed by 0–10% $CH_3OH$ in 0.02% HOAc in $H_2O$ gave 88 mg (33%) of the title compound after lyophilization. IR (KBr) 3400, 2980, 2940, 1750, 1570 cm$^{-1}$. $^1$H NMR ($CDCl_3/CD_3OD$) δ1.03(t,3,J=7Hz,C18), 1.89(q,2,J=7Hz,C19), 2.00(s,3,HOAc), 3.03(m,2,CH$_2$NH), 3.75 (m,2,CH$_2$OH), 4.49(s,ArCH$_2$NH), 5.24(s,2,C5), 5.30(d,1,J=16,C17), 5.70(d,1,J=16Hz,C17), 7.41(d,1,J=8Hz,C11), 7.61(s,1,C14), 8.00 (d,1,J=8Hz,C12), 8.48(s,1,C7). Calcd for $C_{23}H_{23}N_3O_6$ HOAc 1⅞ $H_2O$ (mw=531.3): C,56.52; H,5.83; N,7.91. Fd.: C,56.07; H,5.40; N,8.27.

EXAMPLE 8

Preparation of (20 S) 9-Trimethylammoniummethyl-10-hydroxycamptothecin Methanesulfonate Salt 9-Dimethylaminomethyl-10-hydroxycamptothecin acetate salt (65 mg, 0.14 mmol), prepared as described in Example 3, was dissolved in $CH_2Cl_2$ (ca. 70 mL) and filtered. The filtrate was combined with methyl methanesulfonate (1 mL), cooled and partially concentrated under a stream of argon (Ar). After 4 hr the solvent was concentrated to ½ volume and cooled. The precipitate was filtered, dissolved in $H_2O$ (10 mL), washed with EtOAc (3×10 mL) and then petroleum ether (10 mL) and lyophilized to give 50 mg (60%) of the title compound. IR (KBr) 3400, 2950, 2900, 1760, 1660, 1600 cm$^{-1}$. $^1$H NMR ($CDCl_3/CD_3OD$) δ1.03(d,3,J=7Hz,C18), 2.01(q,2,J=7Hz,C19), 2.78 (s,>3,$CH_3SO_3$), 2.94(s,9,N(CH$_3$)$_3$), 4.72(s,2,ArCH$_2$N), 5.20(s,2,C5), 5.22(d,1,J=16Hz,C17), 5.67(d,1,J=16Hz,C17), 7.62(d,J=7Hz,C11), 7.71(s,C14), 8.16(d,1,J=7Hz,C12), 8.89(s,1,C7). Calcd. for $C_{24}H_{25}N_3O_5 \cdot 1\frac{1}{2} CH_3H_2O$ (mw=615.7): C,49.74; H,5.72; N,6.82. Fd.: C,49.36; H,5.15; N,7.53.

EXAMPLE 9

Preparation of (20 S) 9-Formyl-10-hydroxycamptothecin

10-Hydroxycamptothecin (100 mg, 0.27 mmol), prepared as described in Example 2, hexamethylenetetraamine (0.80 g, 5.5 mmol) and trifluoroacetic acid (TFA) (15 mL) were refluxed under argon for 20 h. The reaction was concentrated, combined with $H_2O$ (15 mL) and stirred for 1 hr. $H_2O$ (75 mL) was added and the pH was adjusted to 8.4 by the addition of $NaHCO_3$. The aq. phase was washed with EtOAc (3×75 mL), acidified to pH 1.5 with 3 N HCl and then extracted with EtOAc (5×75 mL). The combined organic extracts were washed with 1N HCl (5×75 mL), $H_2O$ (75 mL), and saturated aqueous NaCl (25 mL), and concentrated. The residue was then purified by flash chromatography (1 cm×15 cm silica with the crude material preabsorbed on a 1 cm×1 cm plug of $Na_2SO_4$). The product was eluted with 1% $CH_3OH$ in $CH_2Cl_2$ to give 50 mg (47%) of the title compound. An analytically pure sample was obtained by fractionally precipitating from approximately 25% $CH_3OH$ in $CH_2Cl_2$ by slowly cooling and concentrating under a stream of nitrogen. IR (KBr) 3400, 3100, 2950, 1755, 1660, 1600 $cm^{-1}$. $^1H$ NMR ($CCl_3D/CD_3OD$) $\delta 1.04$ (t,3,J=7Hz,C18), 1.96 (d,2,J=7Hz C19), 5.32 (d,1,J=14Hz, C17), 5.33 (s,2,C5). 5.68 (d,1,J=14Hz, C17), 7.50 (d,1,J=9Hz,C11). 7.67 (s,1,C14), 8.33 (d,1,J=9Hz,C12); 9.34 (s,1,C7), 10.85 (s,1,CHO). Calcd for $C_{21}H_{16}N_2O_6 l H_2O$ (mw=410.38): C,61.46; H,4.42; N,6.83. Fd: C,61.09; H,4.17; N,6.52.

EXAMPLE 10

Preparation of (20 S) 9-Cyclopropylaminomethyl-10-hydroxycamptothecin Hydrochloride salt A mixture of 10-hydroxycamptothecin (254 mg, 0.7 mmol), prepared as described in Example 2, 37% aqueous formaldehyde (1.0 mL), cyclopropylamine (400 mg, 0.7 mmol) in glacial acetic acid (16 mL) and ethanol (8 mL) was stirred overnight at ambient temperature and concentrated in vacuo to dryness. The residue was titurated with water, filtered and dried to give 260 mg (75% yield) of the named compound as an acetate salt which was converted to the named hydrochloride salt by triturating with 0.1 N HCl. Anal ($C_{24}H_{23}N_3O_5 \cdot HCl \cdot 3H_2O$). Calcd.: C, 55.01; H, 5.57; N, 8.02. Found: C, 54.94; H, 5.18, N, 8.18. $^1H$ NMR ($D_2O$) $\delta 0.96$ (m, 7), 2.1 (m, 2), 2.8 (m, 1), 4.6 (s, 2), 4.8 (s, 2), 5.2 (s, 2), 7.2 (s, 1), 7.5 (q, 2), 8.6 (s, 1).

EXAMPLE 11

Preparation of (20 S) 9-Ethoxymethyl-10-hydroxycamptothecin

A mixture of 10-hydroxycamptothecin (364 mg, 1.0 mmol), prepared as described in Example 2, dimethylamine hydrochloride (90 mg, 1.1 mmol) and 37% aqueous formaldehyde (1.5 mL) was refluxed in 95% ethanol (25 mL) for 5½ hrs. The reaction was concentrated to a small volume and the precipitated product was collected and dried. Purification by silica gel chromatography eluting with 3% MeOH in $CH_2Cl_2$ gave 85 mg (20% yield) of the named compound. Anal. ($C_{23}H_{22}N_2O_6$). Calcd.: C, 62.08; H, 5.27; N, 6.29. Found: C, 61.80; H, 5.22; N, 6.12. FAB mass spectrum: m/e 423 (MH+). $^1H$ NMR (DMSO) $\delta 0.85$ (t, 3), 1.1 (t, 3), 1.9 (m, 2), 3.5 (s, 2), 4.8 (s, 2), 5.2 (s, 2), 5.4 (s, 2), 7 2 (s, 1), 7.7 (m, 2), 8.6 (s, 1).

EXAMPLE 12

Preparation of (20 S) 9-(N-Methylanilinomethyl)-10-hydroxycamptothecin

A mixture of 10-hydroxycamptothecin (254 mg, 0.7 mmol), prepared as described in Example 2, 37% aqueous formaldehyde (1.0 mL), N methylaniline (0.75 mL, 0.7 mmol) in glacial acetic acid (16 mL) and ethanol (8 mL) was stirred at ambient temperature for 40 hrs. After concentration to an oil, partial purification was obtained by silica gel chromatography eluting with 1,2 and 3% MeOH in $CH_2Cl_2$. The product fractions still contained N-methylaniline. Further purification was obtained using a silica gel MPLC column, and the product was eluted with 2% MeOH in $CH_2Cl_2$. The product fractions were combined and concentrated in vacuo to give 77 mg (24%) of the named compound as a yellow solid. Anal. ($C_{28}H_{25}N_3O_5 \cdot 1.2 H_2O$). Calcd.: C, 66.58; H, 5.47; N, 8.32. Found: C, 66.97; H, 5.69; N, 7.91. DCI mass spectrum: m/e 484 (MH+). $^1H$ NMR (CDCL3) $\delta 1.0$ (t, 3), 1.9 (m, 2), 2.8 (s, 3), 5.0 (s, 2), 5.2 (s, 2), 5.5 (q, 2), 6.9 (m, 5), 7.5 (s, 1), 7.9 (q, 2), 8.4 (s, 1).

EXAMPLE 13

Preparation of (20 S) 9-Cyclohexylaminomethyl-10-hydroxycamptothecin Hydrochloride salt A mixture of 10-hydroxycamptothecin (364 mg, 1.0 mmol), prepared as described in Example 2, 37% aqueous formaldehyde (1.5 mL), cyclohexylamine (1.3 mL, 10 mmol) in glacial acetic acid (25 mL) and ethanol (12 mL) was stirred overnight at ambient temperature and concentrated in vacuo to dryness. The residue was purified on a reversed phase column (MPLC) eluting with 15% aq. MeOH containing 0.02% glacial acetic acid. The named compound as an acetate salt was obtained after concentration to a small volume and lyophilization (250 mg, 47%). The acetate salt was converted to the named hydrochloride salt by addition of 0.1 N HCl, and the salt was collected by filtration. Anal. ($C_{27}H_{29}N_3O_5 \cdot HCl \cdot 1\frac{1}{2} H_2O$). Calcd.: C, 60.93; H, 6.11, N, 7.89. Found: C, 60.83, H, 5.98; N, 7.75. $^1H$ NMR (DMSO) $\delta 0.9$ (t, 3), 1.0–2.0 (m, 10), 3.1 (s, 1), 4.5 (s, 2), 5.2 (s, 2), 5.4 (s. 2), 7.2 (s, 1), 7.9 (q, 2), 8.9 (s, 1).

EXAMPLE 14

Preparation of (20 S) 9-N,N-Dimethylaminoethyloxymethyl-10-hydroxycamptothecin Hydrochloride Salt A mixture of 9-dimethylaminomethyl-10-hydroxycampthecin free base (100 mg, 0.2 mmol), prepared as described in Example 21, in 2 dimethylaminoethanol (4 mL) containing 3 drops of 3N HCl was heated under argon at 80° C. for 24 hrs. The semi-solid reaction mixture was treated with $H_2O$ (5 mL) and isopropanol (10 mL), stirred and filtered to give 60 mg (59%) of the title compound. Anal ($C_{25}H_{27}N_3O_6 \cdot HCl \cdot 0.5 H_2O$). Calcd.: C, 58.77; H, 5.72; N, 8.25. Found: C, 58.94, H, 4.92; N, 7.90. $^1H$ NMR (DMSO) $\delta 0.9$ (t,3), 1.B5 (m,2), 2.3 (s,6), 3.3 (s,2), 4.1 (s,2), 5.2 (s,2), 5.4 (s,2), 7.3 (s,1), 7.4 (d,1), 8.0 (d,1), 8.7 (s,1)

EXAMPLE 15

Preparation of (20 S) 9-N,N-Dimethylaminoethylthiomethyl-10-hydroxycamptothecin Hydrochloride Salt A mixture of 9-dimethylaminomethyl-10-hydroxycamptothecin hydrochloride salt (100 mg, 0.2 mmol), prepared substantially as described in Example 18, and 2-dimethylaminoethanethiol·HCl (560 mg, 4 mmol) in DMF (13 mL) was heated at 85° C. under argon for 5 hrs. The insoluble solid (excess thiol) was removed by filtration, and the filtrate was concentrated in vacuo to an oily residue which was purified using reversed phase MPLC. The product was eluted using 5% and 10% MeOH in $H_2O$ to give 45 mg (41%) of the title compound as a yellow solid. Anal. ($C_{25}H_{28}N_3O_5S·HCl·3 H_2O$). Calcd.: C, 49.34; H, 5.79; N, 6.90. Found: C, 48.98; H, 5.82; N, 6.54. $^1H$ NMR (D20) 6 1.0 (t,3), 1.9 (m,2), 2.8 (s,6), 4.4 (s,2), 5.3 (s,2), 7.1 (d,1), 7.2 (s,1), 7.6 (d,1), 8.2 (s,1).

EXAMPLE 16

Preparation of (20 S) 9-N,N-Dimethylaminoethylaminomethyl-10-hydroxycamptothecin Dihydrochloride Salt A mixture of 10-hydroxycamptothecin (364 mg, 1.0 mmol) prepared as described in Example 2, N,N-dimethylethylenediamine (100 mg, 1.1 mmol), 37% aqueous formaldehyde (1.5 mL) in glacial acetic acid (25 mL) and ethanol (10 mL) was stirred at room temperature for 64 hrs. The solvents were removed in vacuo, and the solid residue was treated with water (10 mL) and isopropanol (10 mL) containing 3 N HCl (3 mL). The finely precipitated solid was collected, washed with isopropanol and dried to give 218 mg (40% yield) of the title compound. Anal. ($C_{25} H_{28}N_4O_5·2HCl$). Calcd.: C, 55.87; H, 5.63; N, 10.42. Found: C, 55.91; H, 5.72; N, 9.86. $^1H$ NMR (CD3OD) δ1.0 (t,3), 1.9 (m,2), 2.9 (s,6), 4.5 (s,2), 5.1 (m,4), 5.4 (q,2), 7.3 (d,1), 7.5 (s,1), 7.8 (d,1), 8.4 s,1).

EXAMPLE 17

Preparation of (20 R,S)-9-Dimethylaminomethyl-10-hydroxycamptothecin Acetate Salt The title compound is prepared as described in Example 3 except that the starting material is racemic 10-hydroxycamptothecin prepared according to the method of Wani et al., *J. Med. Chem.*, 23, 554 (1980).

EXAMPLE 18

Preparation of (20 S) 9-Dimethylaminoethyl-10-hydroxycamptothecin Monohydrochloride Salt 9-Dimethylaminomethyl-10-hydroxycamptothecin acetate salt, prepared as described in Example 3, which analyzed for 2.5 equivalents of acetic acid and 0.75 equivalents of water (8.5 g, 14.5 mmol based on a molecular weight of 585) was dissolved in 0.1 N hydrochloric acid (170 mL, 17 mmol), lyophilized and pumped under high vacuum for three days to give 8.3 g of the title compound. $^1H$ NMR (CDCl3/CD3OD) δ1.05 (t, 3, J=7.5), 1.98 (q, 2, J=7.5), 2.95 (s, 6), 4.77 (s, 2), 5.33 (s, 2), 5.36 (d, 1, J=16), 5.62 (d, 1, J=16), 7.59 (d, 1, J=9), 7.66 (s, 1), 8.20 (d, 1, J=9), 8.86 (s, 1). Anal. ($C_{23}H_{23}N_3O_5·1HCl·3 H_2O$) Calcd.: C, 53.96; H, 5.91; N, 8.21; Cl, 6.92. Found: C, 53.68; H, 5.61; N, 8.16; Cl, 6.84.

EXAMPLE 19

Preparation of (20 S) 9-Dimethylaminoethyl-10-hydroxycamptothecin Dihydrochloride Salt 9-Dimethylaminomethyl-10-hydroxycamptothecin acetate salt (0.389 g, 1.07 mmol by HPLC analysis), prepared as described in Example 3, was dissolved in 0.4 N HCl (6 mL, 2.4 mmol), lyophilized and pumped under high vacuum for 40 h. to give 0.269 g of the title compound. $H^1$NMR (CDCl3/CD3OD) δ1.05 (t, 3, J=7.5), 1.92 (q, 2 J=7.5), 3.01 (s, 6), 4.85 (s, 2), 5.31 (d, 1, J=16). 5.36 (s, 2), 5.65 (d, 1, J=16), 7.64 (d, 1, J=9), 7.73 (s, 1), 8.23 (d, 1, J=9), 9.07 (s, 1). Anal. ($C_{23}H_{23}N_3O_5·2HCl·3 H_2O$) Calcd.: C, 50.37; H, 5.70; N, 7.66; Cl, 12.93. Found: C, 50.76; H, 5.64; N, 7.57; Cl, 12.61.

EXAMPLE 20

Preparation of (20 S) 9-Dimethylaminoethyl-10-hydroxycamptothecin Sodium Salt

9-Dimethylaminomethyl-10-hydroxycamptothecin acetate salt (100 mg, 0.2 mmol), prepared as described in Example 3, was treated with 0.1 N sodium hydroxide (4.5 mL, 0.45 mmol) and the solution was passed throuqh an HP-20 resin column (2×22 cm). The resin was washed with water (250 mL) and the product was eluted with a 1:1 mixture of water and methanol. Fractions containing the product were combined, concentrated to a small volume and lyophilized to give 98 mg (98%) of title compound IR (nujol) 1600 $cm^{-1}$ (carboxylate). $^1H$ NMR (D2O) δ0.65 (m, 3), 1.8 (m, 2), 2.8 (s. 6), 3.0 (m, 2), 4.21 (s, 2), 4.5 (s, 2), 7.1 (q, 2), 7.2 (s, 1), 7.8 (s, 1). Anal. ($C_{23}H_{24}N_3O_6Na·1.5 H_2O$) Calcd.: C, 56.55; H, 5.57; N, 8.60. Found: C, 56.21; H, 5.65; N, 8.44.

EXAMPLE 21

Preparation of (20 S) 9-Dimethylaminomethyl-10-hydroxycamptothecin Free Base

A mixture of 10-hydroxycamptothecin (728 mg 2.0 mmol), prepared as described in Example 2, in glacial acetic (50 mL), ethanol (20 mL), 37% aqueous formaldehyde (3 mL) and 40% aqueous dimethylamine (3 mL) was stirred at room temperature for 20 h. The solvents were removed under reduced pressure; the residue was heated at 50° under high vacuum for 2 h and triturated with isopropanol (10 mL) to precipitate the title compound (561 mg, 64%) as a yellow solid. FAB mass spectrum: m/e 422 (MH+). $^1H$ NMR (CDCl3/CD3OD) δ1.0 (t, 3), 1.9 (m, 2), 2.5 (s, 6), 4.3 (s, 2), 5.2 (s, 2), 5.4 (q, 2), 7.6 (s, 1), 7.7 (q, 2), 8.5 (s, 1).

EXAMPLE 22

Preparation of the triflurormethylsulfonate (triflate) of (20S) 10-hydroxycamptothecin To a mixture of 10-hydroxycamptothecin, prepared as described in Example 2, (1.44 g, 4.0 mmol) in DMF (40 mL) was added triethylamine (1.2 g, 12 mmol) followed by addition of N-phenyl-trifluoromethanesulfonimide (2.0 g, 6 mmol). The reaction was heated at 50° for 3 hrs. The solvent was removed in vacuo and the residue was triturated with water filtered and dried. A theoretical yield of the crude product was obtained essentially as a single spot on thin layer chromatography (TLC) showing a small origin impurity. A small sample was purified by flash chromatography on silica gel column by eluting the product with 2% MeOH in $CH_2Cl_2$. Anal. ($C_{21}H_{15}N_2O_7SF_3$). Calcd.: C,50.81; H,3.05; N,564N Found, C,51N38; H,3N42; N 4N99N $^1H$ MR ($CDCl_3$) δ1.0 (t,3), 1.9 (m,2), 5.3 (s,2), 5.4 (q,2). 7.7 (S,1), 7.6–7.9 (m,2), 8 2 (d,2), 8.5 (s,1) FAB mass spectrum m/e 497 (MH+), 495 (M-H)−

EXAMPLE 23

Preparation of (20S) 9-Dimethylaminomethylcamptothecin

The trifluoromethanesulfonate of (20S) 9-dimethylaminomethyl-10-hydroxycamptothecin acetate salt was made in situ as follows. A mixture of 9-dimethylaminomethyl-10-hydroxycamptothecin acetate salt, prepared as described in Example 3, (482 mg, 1 mmol) in N,N-dimethylformamide (DMF) under argon (40 mL) was treated with 2,6-lutidine (268 mg, 2.5 mmol) and N-phenyltrifluoromethane sulfonimide (0.54 g, 1.5 mmol). The reaction mixture was was stirred overnight at room temperature. Then, to the above formed triflate was added triethylamine (0.4 mL, 3.0 mmol), palladium acetate (8 mg, 0.04 mmol), triphenylphosphine (20 mg, 0.08 mmol) and concentrated formic acid (0.08 mL, 2 mmol). The reaction was heated at 60° for 8 hrs. The solvent was removed in vacuo and the residue was triturated with a small amount of $H_2O$ and filtered. The dried, crude insoluble solid weighed 550 mg. It was purified by flash chromatography on silica gel column by eluting some starting triflate with triphenylphosphate to yield 25 mg (7%) of 9-methylcamptothecin, 88 mg (20%) of the title compound as free base (4% MeOH in $CH_2Cl_2$), and some trifluromethylsulfonate of 10-hydroxycamptothecin with 10% MeOH in $CH_2Cl_2$. Some of the title compound was converted to the acetate salt by treatment with dilute acetic acid.

Anal. ($C_{25}H_{27}N_3O_6$. 2.5$H_2O$). Calcd.: C, 58.81; H, 6.12; N, 8.23. Found: C, 58.60; H, 5.88; N, 7.88; $^1$HNMR ($CDCl_3$) δ0.9 (t.3). 1.8 (m,2), 2.2 (s,6), 3.7 (s,2), 5.2 (s,2), 5.4 (q.2), 7.3 (d,1), 7.5 (d,1) 7.6 (2,1), 8.0 (d,1), 3 3 (S,1) Mass Spectrum m/e 406 (MH$^{30}$)

EXAMPLE 24

Preparation of 10-Cyanocamptothecin

A solution of tributyltin cyanide (444 mg, 1.4 mmol) and tetrakistriphenylphosphine palladium (276 mg, 0.6 mmol) in 1,2-dichloroethane (20 mL) was heated to reflux under argon for 2 hrs to form a palladium tin-cyanide complex. Then the trifluoromethylsulfonate of 10-hydroxycamptothecin, prepared as described in Example 22, (266 mg, 0.6 mm) was added and refluxing was continued for 3.5 hrs. The reaction was concentrated to ⅓ of its original volume and triturated with an equal volume of diethylether. The precipitated yellow solid was collected and dried. The title compound was obtained in 82% crude yield, 183 mg. After purification by flash chromatography, the title compound eluted with 2% MeOH in $CH_2Cl_2$ and 115 mg (67%) was obtained.

Anal. ($C_{21}H_{15}N_3O_4$. ½$H_2O$ Calcd.: C, 65.96; H, 4.22; N, 10.99.

Found: C, 65.89; H,4.06; N, 10.66. $^1$HNMR ($CDCl_3$-$MeOD_4$) δ1.0 (t,3), 1.9 (m,2), 5.4 (s,2), 5.5 (q,2), 7.7 (s,1), 7.7 8.4 (m,3), 8.6 (s,1).

Mass spectrum m/e 374(MH+)

EXAMPLE 25

Preparation of (20S) 10-Formylcamptothecin

A flame dried flask was charged with the trifluromethylsulfonate of 10-hydroxycamptothecin, prepared as described in Example 22, (100 mg, 0.22 mmol), freshly distilled tetrahydrofuran (THF) (10 mL) and tetrakis triphenylphosphine palladium (10 mg, 9 mmol). Carbon monoxide (CO) was bubbled into the reaction for 3 min, and then the reaction mixture was stoppered with a CO balloon and immersed in an oil bath at 50°. While stirring and using a syringe pump, a solution of $Bu_3SnH$ (0.73 mL) in dry THF (3 mL) was added dropwise over a 4 hr period. After this time, the solvent was removed in vacuo, and the residue was purified by flash chromatography (1–2% $CH_3OH$, $CH_2Cl_2$) followed by final purification using a Chromatotron (Harrison Research, Palo Alto, Calif.). The title compound was eluted with 2% MeOH in $CH_2Cl_2$, 20 mg (24%).

Anal.: ($C_{21}$, $H_{16}$, $N_2O_{5.1\frac{1}{3}}$ $H_2O$) Calcd. C, 61.84; H, 4.69; N, 6.86.

Found: C, 61.83; H, 4.53; N, 6.37. $^1$ NMR ($CDCl_3$) δ0.9 (t, 3), 1.9 (m, 2). 5.3 (split s, 2), 5.4 (q, 2), 7.7 (d, 1), 7.8 8.3 (m, 3), 8.5 (s, 1), 9.9 (s 1) Mass spectrum m/e 377 (MH+).

EXAMPLE 26

Preparation of (20S) 10-Aminomethylcamptothecin Acetate salt

A solution of 10-cyanocamptothecin, prepared as described in Example 24, (160 mg, 0.4 mmcl) in glacial acetic acid (45 mL) was treated with activated raney nickel and hydrogenated at 10 psi (1785.8 grams/cm) for 7 hrs. The catalyst was removed by filtration through supercel and the filtrate was concentrated in vacuo. The solid residue was purified by medium pressure chromatography on reversed phase column by eluting the product with 10% MeOH in water. After freeze drying, 25 mg (15%) of the hygroscopic title compound was obtained.

Anal.: ($C_{23}H_{23}N_3O_{6.6}$ $H_2O$) Calcd.: C, 50.63; H, 6.46; N, 7.73.

Found: C, 50.11; H, 6.57; N, 7.64.

$^1$H NMR ($D_2O$) δ1.0 (t, 3), 1.9 (m, 2), 4.3 (s, 2), 5.2 (s, 2), 5.4 (s, 2), 7.5 (s, 1), 7.7–8.1 (m, 3), 8.6 (s, 1).

EXAMPLE 27

Preparation of (20S) 10-Aminomethylcamptothecin acetate salt

A solution of 10-cyanocamptothecin, prepared as described in Example 24, (160 mg, 0.42 mmol) in glacial acetic acid (45 mL) was treated with activated Raney ® nickel and hydrogenated at 10 psi (1785.8 grams/cm) for 7 hrs. The catalyst was filtered throuqh supercel (95% $SiO_2$), concentrated in vacuo and purified on a reversed phase column. The product eluted in 10% MeOH $H_2O$ (containing 0.02% acetic acid). After pooling the fractions, concentrating to a small volume and lyophilizing, the title compound was obtained, 26 mg (14%).

Anal.: ($C_{23}H_{23}N_3O_6$). Calcd.: C, 50.53; H, 6.46; N, 7.73.

Found: C, 50.11; H, 6.57; N, 7.64.

¹HNMR (D₂O/MeOD₄) δ1.0(t,3), 2.0(m,2), 4.3(s,2), 5.2(s,2), 5.5(s,2), 7.5(s,1), 8.0(m,3), 8.6(s,1).

EXAMPLE 28

Preparation of (20S) 9-Morpholinomethylcamptothecin

A 1 mmol solution of the trifluoromethylsulfonate of 10-hydroxy-9-morpholinomethylcamptothecin, prepared as described in Example 23, in dry DMF (25 mL) was treated with triethylamine (0.4 mL), Pd (acetic acid)₂ (8 mg, 0.04 mmol), φ₃P (20 mg, 0.08 mmol) and 99% formic acid (0.08 mL, 2 mmol). The reaction was heated under argon at 60° for 6 hrs, concentrated in vacuo and treated with water. Both the desired title compound and the major by-product, 9-methylcamptothecin, precipitated out (300 mg) and were collected by filtration silica gel flash chromatography purification. 9-methyl camptothecin was isolated by elution in 1% MeOH in CH₂Cl₂ (45 mg, 13%). Elution with 2% MeOH in CH₂Cl₂ gave the title compound (93 mg, 20%).

Anal.: (C₂₅H₂₅N₃O₅·½ H₂O) Calcd.: C, 65.78; H, 5.74; N, 9.20.

Found: C, 65.87; H, 5.96; N. 9.00.

Mass spectrum m/e 448 (MH+)

¹HNMR (CDCl₃/MeOD₄) δ1.0 (t,3), 2.0 (m,2), 2.5 (m,4), 3.7 (m,4), 4.0 (s,2), 5.3 (3,2), 5.6 (q,2), 7.5 (d,1), 7.6 (s.1), 7.7(d,1) 8.2 (d,1), 9.0 (s,1).

EXAMPLE 29

Preparation of (20S) 10-Hydroxy-9-cyanomethylcamptothecin

A mixture of 9-trimethylammoniummethyl-10-hydroxycamptothecin methanesulfonate salt, prepared as described in Example 8, (0.42g, 0.8 mmol) in 95% EtOH (35 mL) and sodium cyanide (1.26g, 25 mmol) was refluxed under argon for 3 hrs. Solvent was removed in vacuo, water was added (20 mL) and the pH adjusted to 1.5 with 3 N HCl. The precipitated crude solid was collected and dried. Purification was accomplished by flash silica gel column chromatography. The product was eluted with 4% and 5% MeOH in CH₂Cl₂ which gave 110 mg (33%) of the title compound.

Anal. (C₂₂H₁₇N₃O₅·1¾ H₂O). Calcd.: C, 60.75; H, 4.58; N, 9.66.

Found: C, 60.63; H, 4.64; N, 9.60.

¹HNMR (CDCl₃/MeOD₄) δ0.9 (t,3), 1.8 (m,2), 4.2 (s,2), 5.2 (s,2), 5.3 (q,2), 7.5 (d,1), 7.6 (s,1), 7.9 (d,1), 8.4 (s,1).

EXAMPLE 30

Preparation of (20S) 10-Hydroxy-9-aminoethylcamptothecin Acetate Salt

A solution of 60 mg (0.15 mm) of 10-hydroxy-9-cyanomethylcamptothecin, prepared as described in Example 29, in glacial acetic acid (30 mL) was treated with approximately 1 gm (wet weight) of activated Raney® nickel and hydrogenated at 10 psi (1785.8 grams/cm) for 6 hrs. The catalyst was removed by filtration and the filtrate was concentrated in vacuo to a solid residue. The concentrated filtrate was then dissolved in water and purified by reverse phase column chromatography by eluting the product with 10% MeOH in water (containing 0.02% glacial acetic acid). The appropriate fractions were collected, concentrated to a small volume and freeze dried overnight yielding 23 mg (33%) of the title compound.

Anal.: C₂₄H₂₅N₃O₄·10 H₂O) Calcd.: C, 43.90; H, 6.90; N 6.38.

Found: C, 43.82; H, 6.89; N, 5.79.

¹H NMR (DMSO-d₆) δ 0.9 (t,3), 1.9 (m,2), 3.2 (s,2), 5.0(3,2), 5.1(s,2), 5.4(s,2), 7 2(s,1), 7.5(q,2), 8.4(s,1).

III. Pharmaceutical Composition Examples

EXAMPLE A

Parenteral Composition

To prepare a parenteral pharmaceutical composition of this invention suitable for administration by injection, 100 mg of a water soluble salt of a compound of Formula (I) is mixed with 10 ml of 0.9% sterile saline, and the mixture is incorporated into a dosage unit form suitable for administration by injection.

EXAMPLE B

Oral Composition

To prepare an oral pharmaceutical composition of this invention, 100 mg of a compound of Formula (I) is mixed with 750 mg of lactose, and the mixture is incorporated into an oral dosage unit form, such as a hard gelatin capsule, which is suitable for oral administration.

What is claimed is:

1. A compound of the formula:

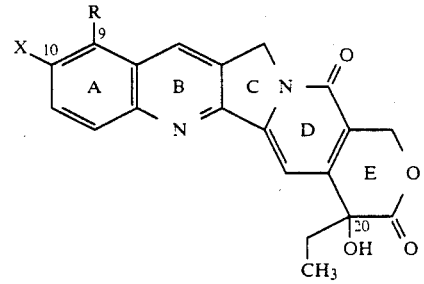

wherein:
X is hydroxy; hydrogen; —CH₂NH₂; or formyl;
R is hydrogen when X is CH₂NH₂ or formyl; or R is —CHO or —CH₂R¹ when X is hydrogen or hydroxy;
R¹ is —O—R²; —S—R²; —CH₂NH₂; cyano; —N—R²(R³); or —N⁺—R²(R³)(R⁴), provided that when R¹ is —N⁺—R²(R³)(R⁴) the compound is associated with a pharmaceutically acceptable anion;
R², R³ and R⁴ are the same or different and are selected from H; C₁₋₆ alkyl; C₂₋₆ hydroxyalkyl; C₁₋₆ dialkylamino-C₂₋₆ alkyl; C₁₋₆ alkylamino-C₂₋₆ alkyl; C₂₋₆ aminoalkyl or a 3–7 member unsubstituted carbocyclic ring; and
when R¹ is —N—R²(R³), the R² and R³ groups may be combined together with the nitrogen atom to which they are bonded to form a heterocyclic ring provided that such heterocyclic ring is selected from morpholino, N-methylpiperazinyl, or 4'-piperidinopiperidinyl;
or a pharmaceutically acceptable salt, hydrate or solvate thereof.

2. The compound of claim 1 wherein X is hydroxy and R is dimethylaminomethyl, N-morpholinomethyl, N-methylpiperazinylmethyl, (4'-piperidine)N-piperidinylmethyl, (2'-hydroxyethyl)aminomethyl, trimethylammoniummethyl, cyclohexylaminomethyl, N-methylanilinomethyl, ethoxymethyl, cyclopropylaminomethyl, N,N-dimethylaminoethyloxymethyl, N,N-dimethylaminoethylthiomethyl, N,N-dimethylaminoethylaminomethyl, cyanomethyl, aminoethyl or formyl; or wherein R is hydrogen and X is formyl or aminomethyl; or wherein X is hydrogen and R is dimethylaminomethyl or N-morpholinomethyl.

3. The compound of claim 1 which is the S-isomer.

4. The compound of claim 1 which is the racemic mixture.

5. The compound of claim 3 wherein X is hydroxy and R is dimethylaminomethyl.

6. The compound of claim 5 which is the acetate salt.

7. The compound of claim 5 which is the monohydrochloride, dihydrochloride or sodium salt.

8. The compound of claim 3 wherein X is hydroxy and R is trimethylammoniummethyl.

9. The compound of claim 3 wherein X is hydroxy and R is N-methylpiperazinylmethyl.

10. The compound of claim 3 wherein X is hydroxy and R is N-methylanilinomethyl.

11. The compound of claim 3 wherein X is hydroxy and R is cyclohexylaminomethyl.

12. The compound of claim 3 wherein X is hydroxy and R is N,N-dimethylaminoethyloxymethyl.

13. The compound of claim 3 wherein X is hydroxy and R is cyanomethyl.

14. The compound of claim 3 wherein X is hydroxy and R is morpholinomethyl.

15. The compound of claim 3 wherein X is hydroxy and R is aminomethyl.

16. The compound of claim 3 wherein X is hydroxy and R is cyclopropylaminomethyl.

17. A pharmaceutical composition comprising an effective tumor cell growth-inhibiting amount of an active ingredient and an inert pharmaceutically acceptable carrier or diluent, wherein said composition is useful for inhibiting the growth of animal tumor cells sensitive to the active ingredient, and wherein the active ingredient is a compound of the formula:

[Structure]

X is hydroxy; hydrogen; —$CH_2NH_2$; or formyl;
R is hydrogen when X is $CH_2NH_2$ or formyl; or R is —CHO or —$CH_2R^1$ when X is hydrogen or hydroxy;
$R^1$ is —O—$R^2$; —S—$R^2$; —$CH_2NH_2$; cyano; —N—$R^2(R^3)$; or —$N^+$—$R^2(R^3)(R^4)$, provided that when $R^1$ is —$N^+$—$R^2(R^3)(R^4)$ the compound is associated with a pharmaceutically acceptable anion;
$R^2$, $R^3$ and $R^4$ are the same or different and are selected from H; $C_{1-6}$ alkyl; $C_{2-6}$ hydroxyalkyl; $C_{1-6}$ dialkylamino-$C_{2-6}$ alkyl; $C_{1-6}$ alkylamino-$C_{2-6}$ alkyl; $C_{2-6}$ aminoalkyl or a 3-7 member unsubstituted carbocyclic ring; and when $R^1$ is —N—$R^2(R^3)$, the $R^2$ and $R^3$ groups may be combined together with the nitrogen atom to which they are bonded to form a heterocyclic ring provided that such heterocyclic ring is selected from morpholino, N-methylpiperazinyl, or 4'-piperidinopiperidinyl;

or a pharmaceutically acceptable salt, hydrate or solvate thereof.

18. The composition of claim 17 wherein X is hydroxy and R is dimethylaminomethyl, N-morpholinomethyl, N-methylpiperazinylmethyl, (4'-piperidine)N-piperidinylmethyl, (2'-hydroxyethyl)aminomethyl, trimethylammoniummethyl, cyclohexylaminomethyl, N-methylanilinomethyl, ethoxymethyl, cyclopropylaminomethyl, N,N-dimethylaminoethyloxymethyl, N,N-dimethylaminoethylthiomethyl, N,N-dimethylaminoethylaminomethyl, cyanomethyl, aminoethyl or formyl; or wherein R is hydrogen and X is formyl or aminomethyl; or wherein X is hydrogen and R is dimethylaminomethyl or N-morpholinomethyl.

19. The composition of claim 17 which is the S-isomer.

20. The composition of claim 17 which is the racemic mixture.

21. The composition of claim 19 wherein X is hydroxy and R is dimethylaminomethyl.

22. The composition of claim 21 which is the acetate salt.

23. The composition of claim 21 which is the monohydrochloride, dihydrochloride or sodium salt.

24. The composition of claim 17 which is in oral dosage form.

25. The composition of claim 17 which is in parenteral dosage form.

26. A method of inhibiting the growth of animal tumor cells sensitive to a compound of the formula:

[Structure]

wherein:
X is hydroxy; hydrogen; —$CH_2NH_2$; or formyl;
R is hydrogen when X is $CH_2NH_2$ or formyl; or R is —CHO or —$CH_2R^1$ when X is hydrogen or hydroxy;
$R^1$ is —O—$R^2$; —S—$R^2$; —$CH_2NH_2$; cyano; —N—$R^2(R^3)$; or —$N^+$—$R^2(R^3)(R^4)$, provided that when $R^1$ is —$N^+$—$R^2(R^3)(R^4)$ the compound is associated with a pharmaceutically acceptable anion;
$R^2$, $R^3$ and $R^4$ are the same or different and are selected from H; $C_{1-6}$ alkyl $C_{2-6}$ hydroxyalkyl; $C_{1-6}$ dialkylamino-$C_{2-6}$ alkyl; $C_{1-6}$ alkylamino-$C_{2-6}$ alkyl; $C_{2-6}$ aminoalkyl or a 3-7 member unsubstituted carbocyclic ring; and
when $R^1$ is —N—$R^2(R^3)$, the $R^2$ and $R^3$ groups may be combined together with the nitrogen atom to which they are bonded to form a heterocyclic ring provided that such heterocyclic ring is selected from morpholino, N-methylpiperazinyl, or 4'-piperidinopiperidinyl;

or a pharmaceutically acceptable salt, hydrate or solvate thereof, wherein such method comprises administering to an animal afflicted with said tumor cells, an effective, tumor cell growth inhibiting amount of such compound.

27. The method of claim 26 wherein X is hydroxy and R is dimethylaminomethyl, N-morpholinomethyl, N-methylpiperazinylmethyl, (4'-piperidine)N-piperidinylmethyl, (2'-hydroxyethyl)aminomethyl, trimethylammoniummethyl, cyclohexylaminomethyl, N-methylanilinomethyl, ethoxymethyl, cyclopropylaminomethyl, N,N-dimethylamino ethyloxymethyl, N,N-dimethylaminoethylthiomethyl, N,N-dimethylaminoethylaminomethyl, cyanomethyl, aminoethyl or formyl; or wherein R is hydrogen and X is formyl or aminomethyl; or wherein X is hydrogen and R is dimethylaminomethyl or N morpholinomethyl.

28. The method of claim 26 which is the S-isomer.

29. The method of claim 26 which is the racemic mixture.

30. The method of claim 28 wherein X is hydroxy and R is dimethylaminomethyl.

31. The method of claim 30 which is the acetate salt.

32. The method of claim 30 which is the monohydrochloride, dihydrochloride or sodium salt.

33. The method of claim 26 wherein the compound is administered orally.

34. The method of claim 26 wherein the compound is administered parenterally.

35. A compound of the formula

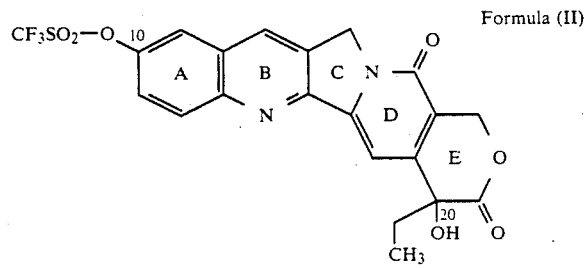

Formula (II)

* * * * *

UNITED STATES PATENT AND TRADEMARK OFFICE

CERTIFICATE EXTENDING PATENT TERM
UNDER 35 U.S.C. § 156

PATENT NO.      :   5,004,758

ISSUED          :   April 2, 1991

INVENTOR(S)     :   Boehm et al.

PATENT OWNER    :   SmithKline Beecham Corporation

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 786 days from April 2, 2008, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 27th day of August 1998.

Bruce A. Lehman
Assistant Secretary of Commerce and
  Commissioner of Patents and Trademarks

UNITED STATES PATENT AND TRADEMARK OFFICE
CERTIFICATE OF CORRECTION

PATENT NO. : 5,004,758
DATED : April 2, 1991
INVENTOR(S) : Boehm, et. al.

It is certified that error appears in the above-identified patent and that said Letters Patent is hereby corrected as shown below:

In column 31, line 34, before "Unless", insert -- NMR spectra are given in $\delta$ units --;

In column 33, line 61, after "Hz,", insert -- ,C19--;

In column 35, line 4, delete "$CH_3H_2O$", and insert therefor -- $CH_3SO_3H$ --;

In column 36, line 68, delete "1.B5", and substitute therefor -- 1.05 --;

In column 37, line 55, delete "9-Dimethylaminoethyl-10-hydroxycamptothecin" and substitute therefor -- 9-Dimethylaminomethyl-10-hydroxycamptothecin --;

In column 38, line 7, delete "9-Dimethylaminoethyl-10-hydroxycamptothecin" and substitute therefor -- 9-Dimethylaminomethyl-10-hydroxycamptothecin --;

In column 38, line 25, delete "9-Dimethylaminoethyl-10-hydroxycamptothecin" and substitute therefor -- 9-Dimethylaminomethyl-10-hydroxycamptothecin --;

In column 39, line 47, delete "($MH^{30}$)", and substitute therefor -- ($MH^+$) --;

In column 40, line 38, delete "(1785.8 grams/cm)", and substitute therefor --

UNITED STATES PATENT AND TRADEMARK OFFICE
CERTIFICATE OF CORRECTION

PATENT NO. : 5,004,758
DATED : April 2, 1991
INVENTOR(S) : Boehm, et. al.

It is certified that error appears in the above-identified patent and that said Letters Patent is hereby corrected as shown below:

--703.1 g/cm$^2$)--; and

In column 40, line 59, delete "(1785.8 grams/cm)", and substitute therefor -- --703.1 g/cm$^2$)--.

In column 41, line 28, delete "(3,2)", and substitute therefor -- (s,2) --;

In column 42, line 1, delete "C$_{24}$H$_{25}$N$_3$O$_u$ ·10 H$_2$O)", and substitute therefor -- C$_{24}$H$_{25}$N$_3$O$_7$ ·10 H$_2$O)--; and In column 42, line 5, delete "5.0(3,2)", and substitute therefor -- 5.0(s,2)--.

Signed and Sealed this

Twenty-fourth Day of October, 2000

Attest:

Q. TODD DICKINSON

*Attesting Officer*   *Director of Patents and Trademarks*